(12) United States Patent
Hibner

(10) Patent No.: US 11,364,047 B2
(45) Date of Patent: *Jun. 21, 2022

(54) SURGICAL INSTRUMENT WITH DUAL MODE ARTICULATION DRIVE

(71) Applicant: Ethicon LLC, Guaynabo, PR (US)

(72) Inventor: John A. Hibner, Mason, OH (US)

(73) Assignee: Cilag GmbH International, Zug (CH)

( * ) Notice: Subject to any disclaimer, the term of this patent is extended or adjusted under 35 U.S.C. 154(b) by 39 days.

This patent is subject to a terminal disclaimer.

(21) Appl. No.: 16/429,127

(22) Filed: Jun. 3, 2019

(65) Prior Publication Data

US 2019/0321069 A1    Oct. 24, 2019

Related U.S. Application Data

(63) Continuation of application No. 15/088,357, filed on Apr. 1, 2016, now Pat. No. 10,492,819.

(51) Int. Cl.
*A61B 17/32* (2006.01)
*A61B 17/29* (2006.01)
*A61B 17/00* (2006.01)

(52) U.S. Cl.
CPC .............. *A61B 17/320092* (2013.01); *A61B 2017/0023* (2013.01); *A61B 2017/0046* (2013.01);
(Continued)

(58) Field of Classification Search
CPC ...... A61B 17/00234; A61B 17/320092; A61B 2017/003; A61B 2017/00318; A61B 2017/00371
See application file for complete search history.

(56) References Cited

U.S. PATENT DOCUMENTS

| | | |
|---|---|---|
| 5,322,055 A | 6/1994 | Davison et al. |
| 5,873,873 A | 2/1999 | Smith et al. |

(Continued)

FOREIGN PATENT DOCUMENTS

| | | |
|---|---|---|
| CN | 103687551 A | 3/2014 |
| CN | 105310736 A | 2/2016 |
| WO | WO 2015/100287 | 7/2015 |

OTHER PUBLICATIONS

European Communication dated Oct. 18, 2019 for Application No. 17716422.5, 4 pages.

(Continued)

*Primary Examiner* — Ashley L Fishback
(74) *Attorney, Agent, or Firm* — Frost Brown Todd LLC

(57) ABSTRACT

A surgical instrument includes a shaft assembly and an articulation control assembly. The shaft assembly includes an articulation section. The distal end of the shaft assembly is configured to receive an end effector. The articulation section is configured to deflect the end effector from the longitudinal axis. The articulation control assembly includes a first articulation control member, a second articulation control member, and a transmission assembly. The transmission assembly includes a high ratio drive and a low ratio drive. The high ratio drive is configured to drive the articulation section to deflect the end effector at a high rate of articulation in response to actuation of the first articulation control member. The low ratio drive is configured to drive the articulation section to deflect the end effector at a low rate of articulation in response to actuation of the second articulation control member.

20 Claims, 21 Drawing Sheets

(52) U.S. Cl.
CPC ............... *A61B 2017/00477* (2013.01); *A61B 2017/2908* (2013.01); *A61B 2017/320093* (2017.08); *A61B 2017/320094* (2017.08)

(56) References Cited

U.S. PATENT DOCUMENTS

| | | | |
|---|---|---|---|
| 5,897,523 | A | 4/1999 | Wright et al. |
| 5,980,510 | A | 11/1999 | Tsonton et al. |
| 5,989,264 | A | 11/1999 | Wright |
| 6,063,098 | A | 5/2000 | Houser et al. |
| 6,090,120 | A | 7/2000 | Wright et al. |
| 6,325,811 | B1 | 12/2001 | Messerly |
| 6,454,782 | B1 | 9/2002 | Schwemberger |
| 6,589,200 | B1 | 7/2003 | Schwemberger et al. |
| 6,752,815 | B2 | 6/2004 | Beaupre |
| 6,773,444 | B2 | 8/2004 | Messerly |
| 6,783,524 | B2 | 8/2004 | Anderson et al. |
| 6,913,613 | B2 | 7/2005 | Schwarz et al. |
| 7,135,030 | B2 | 11/2006 | Schwemberger et al. |
| 7,621,930 | B2 | 11/2009 | Houser |
| 8,461,744 | B2 | 6/2013 | Wiener et al. |
| 8,517,239 | B2 | 8/2013 | Scheib et al. |
| 8,591,536 | B2 | 11/2013 | Robertson |
| 8,623,027 | B2 | 1/2014 | Price et al. |
| 8,663,220 | B2 | 3/2014 | Wiener et al. |
| 8,668,702 | B2 | 3/2014 | Awtar et al. |
| 8,986,302 | B2 | 3/2015 | Aldridge et al. |
| 9,023,071 | B2 | 5/2015 | Miller et al. |
| 9,095,367 | B2 | 8/2015 | Olson et al. |
| 9,381,058 | B2 | 7/2016 | Houser et al. |
| 9,393,037 | B2 | 7/2016 | Olson et al. |
| 10,342,567 | B2 | 7/2019 | Hibner et al. |
| 10,492,819 | B2 | 12/2019 | Hibner |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2012/0041450 | A1 | 2/2012 | Atwar et al. |
| 2012/0078247 | A1 | 3/2012 | Worrell et al. |
| 2012/0116265 | A1 | 5/2012 | Houser et al. |
| 2013/0289592 | A1 | 10/2013 | Stulen et al. |
| 2014/0005703 | A1 | 1/2014 | Stulen et al. |
| 2015/0080924 | A1 | 3/2015 | Stulen et al. |
| 2015/0141981 | A1 | 5/2015 | Price et al. |
| 2016/0015419 | A1 | 1/2016 | Hibner et al. |

OTHER PUBLICATIONS

International Search Report and Written Opinion dated May 4, 2017 for International Application No. PCT/US2017/024983, 13 pages.
U.S. Appl. No. 61/410,603, filed Nov. 5, 2010.
U.S. Appl. No. 14/258,179, filed Apr. 22, 2014.
Chinese Office Action, Notification of First Office Action, and First Search dated Sep. 27, 2020 for Application No. CN 201780028009. 5, 6 pgs.
Japanese Office Action, Notice of Reasons for Refusal, and Search Report by Registered Search Organization, dated Mar. 23, 2021 for Application No. JP 2018-551141, 13 pgs.
Indian Examination Report dated May 25, 2021 for Application No. IN 201817035919, 6 pgs.

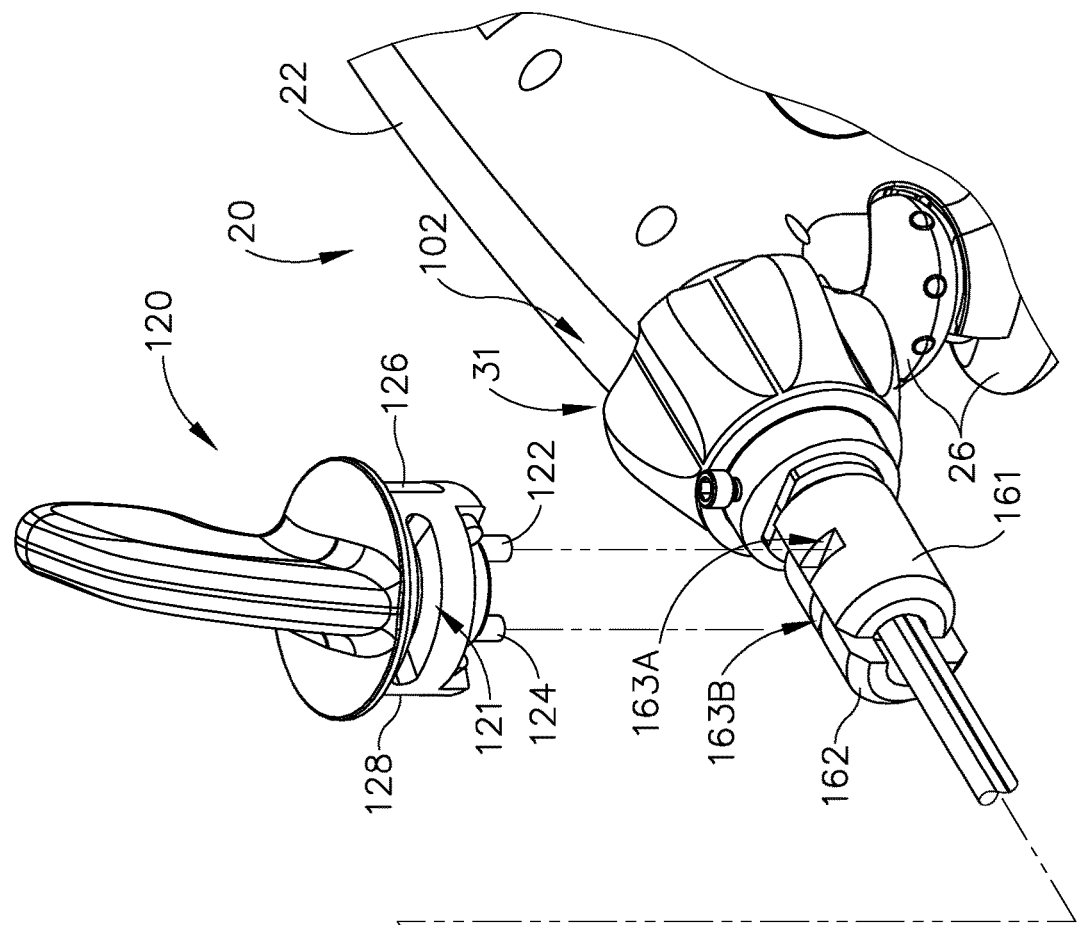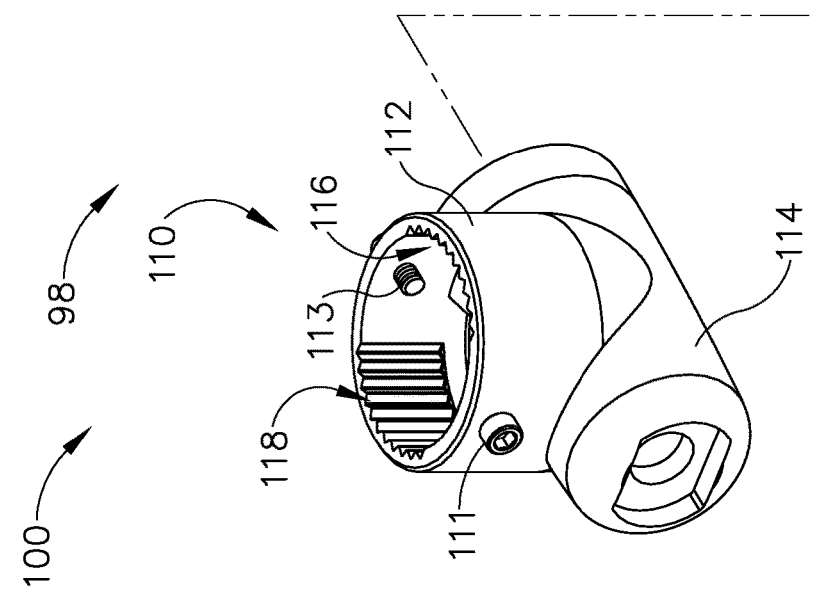
Fig. 9

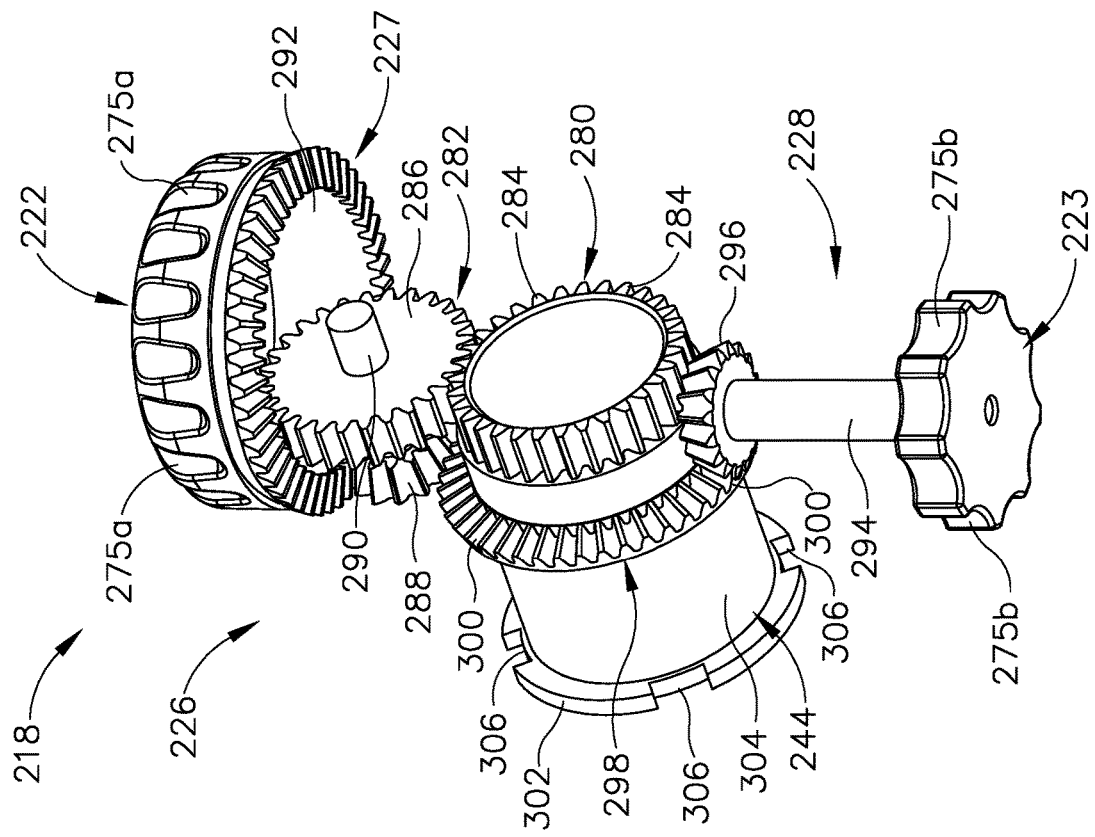
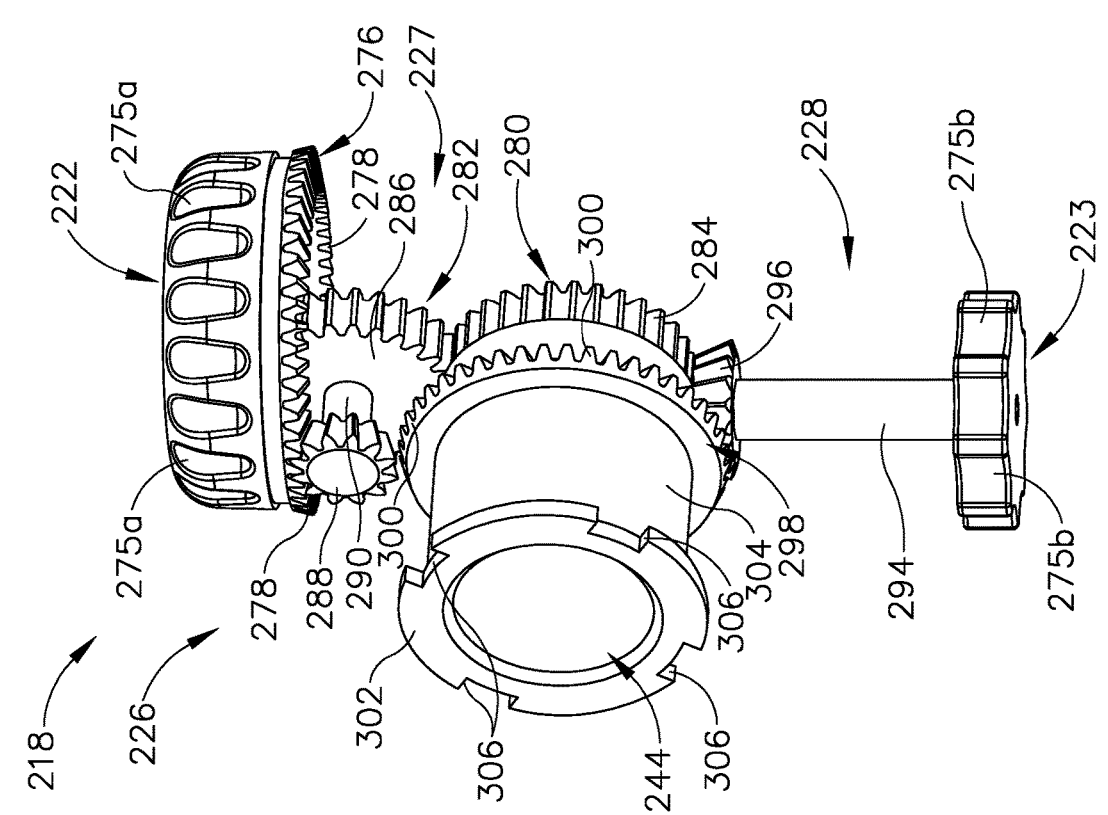

SURGICAL INSTRUMENT WITH DUAL MODE ARTICULATION DRIVE

This application is a continuation of U.S. patent application Ser. No. 15/088,357, entitled "Surgical Instrument with Dual Mode Articulation Drive," filed Apr. 1, 2016.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, now U.S. Pat. No. 9,393,037, issued on Jul. 16, 2016, entitled "Surgical Instruments with Articulating Shafts," the disclosure of which is incorporated by reference herein; U.S. Pub. No. 2014/0005703, entitled "Surgical Instruments with Articulating Shafts," published Jan. 2, 2014, now U.S. Pat. No. 9,408,622, issued on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, now U.S. Pat. No. 9,095,367, issued on Aug. 4, 2015, the disclosure of which is incorporated by reference herein; U.S. Pub. No. 2015/0080924, entitled "Articulation Features for Ultrasonic Surgical Instrument," published Mar. 19, 2015, now U.S. Pat. No. 10,172,636, issued on Jan. 8, 2019, the disclosure of which is incorporated by reference herein; and U.S. patent application Ser. No. 14/258,179, entitled "Ultrasonic Surgical Device with Articulating End Effector," filed Apr. 22, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9 depicts a partially exploded perspective view of an shaft control assembly of the instrument of FIG. 1;

FIG. 20 depicts an upper front perspective view of a dual sensitivity drive of the dual mode articulation control assembly of FIG. 13;

FIG. 21 depicts a lower rear perspective view of the dual sensitivity drive of FIG. 20;

Figure 1:
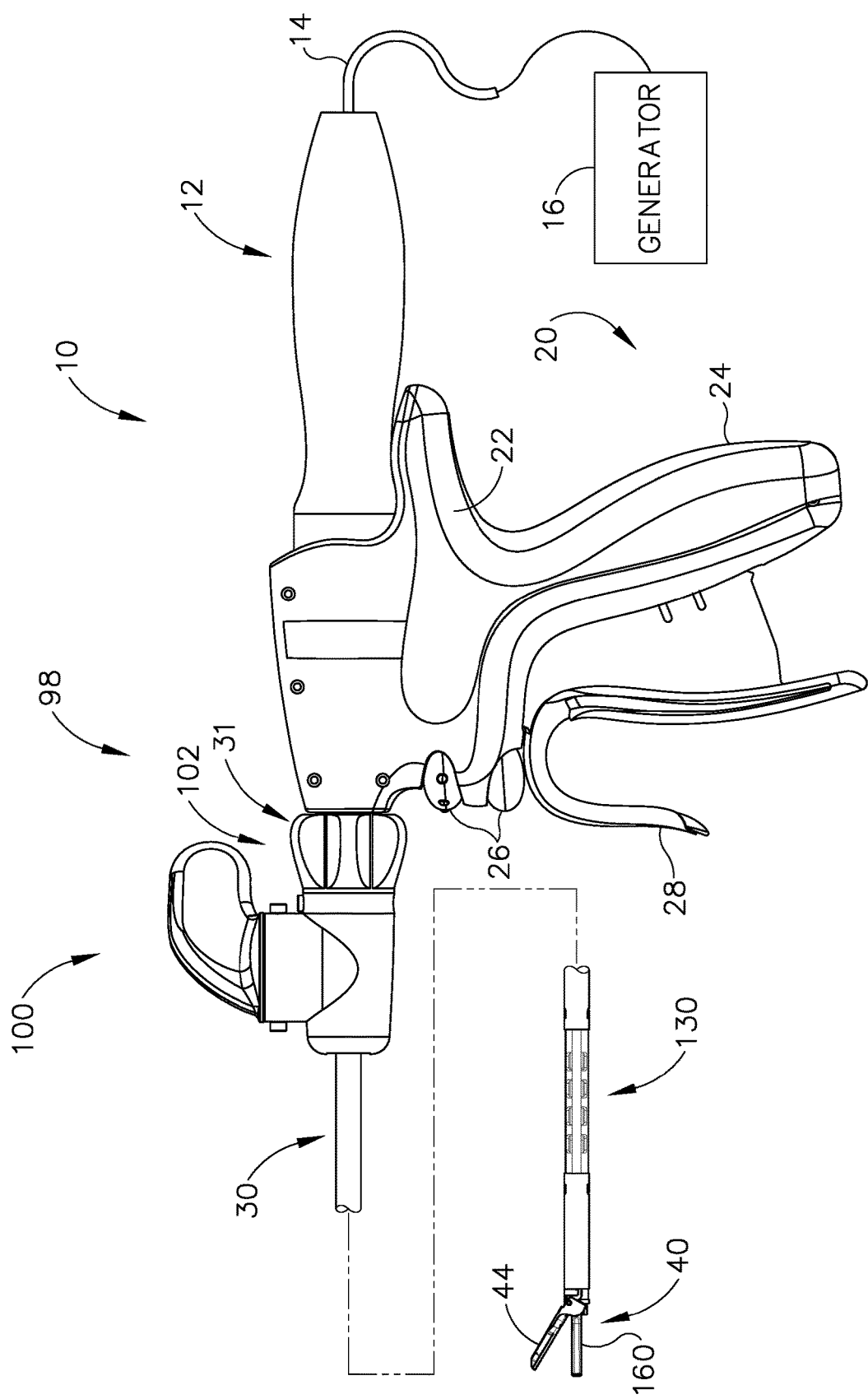
FIG. 1 depicts a side elevational view of a first exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal," "distal," "upper," and "lower" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. The terms "proximal," "distal," "upper," and "lower" are thus relative terms and not intended to unnecessarily limit the invention described herein.

Furthermore, for additional clarity of the disclosure, the terms "high" and "low" are defined herein with respect to transmission ratios of transmission input to transmission output. For example, a "high" transmission ratio results in a predetermined input yielding a relatively "high" transmission output, but with less sensitivity to input. In contrast, a "low" transmission ratio results in the predetermined input yielding a relatively "low" transmission output, but with greater sensitivity to input. It will be appreciated that such concepts similarly apply to "high" and "low" gearing ratios in mechanical transmission assemblies. To this end, the terms "high" and "low" are relative terms and not intended to unnecessarily limit the invention described herein.

I. Exemplary Ultrasonic Surgical Instrument

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN04 or GEN11 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 2:
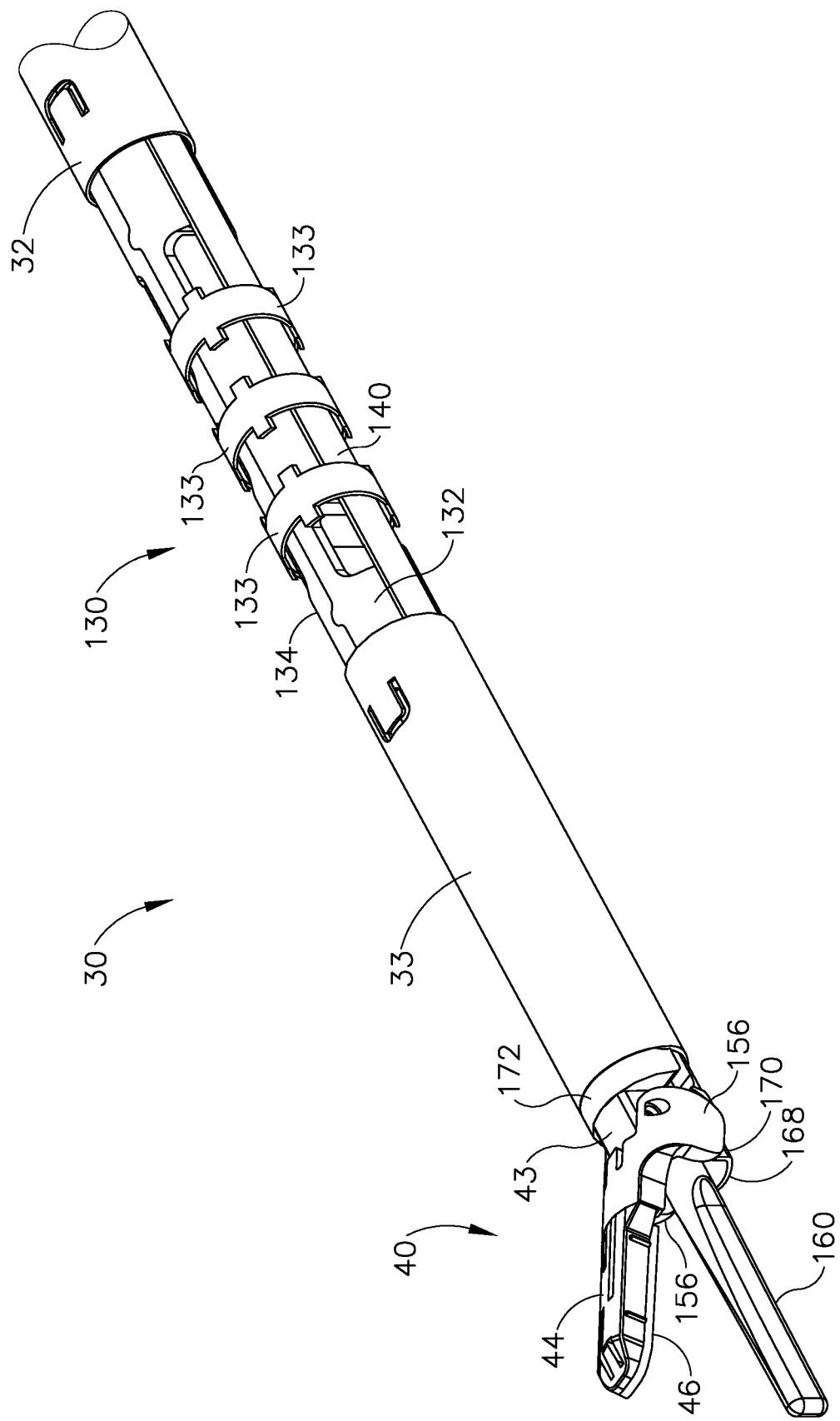
FIG. 2 depicts a perspective view of an articulation section of a shaft assembly and an end effector of the surgical instrument of FIG. 1.
Figure 3:
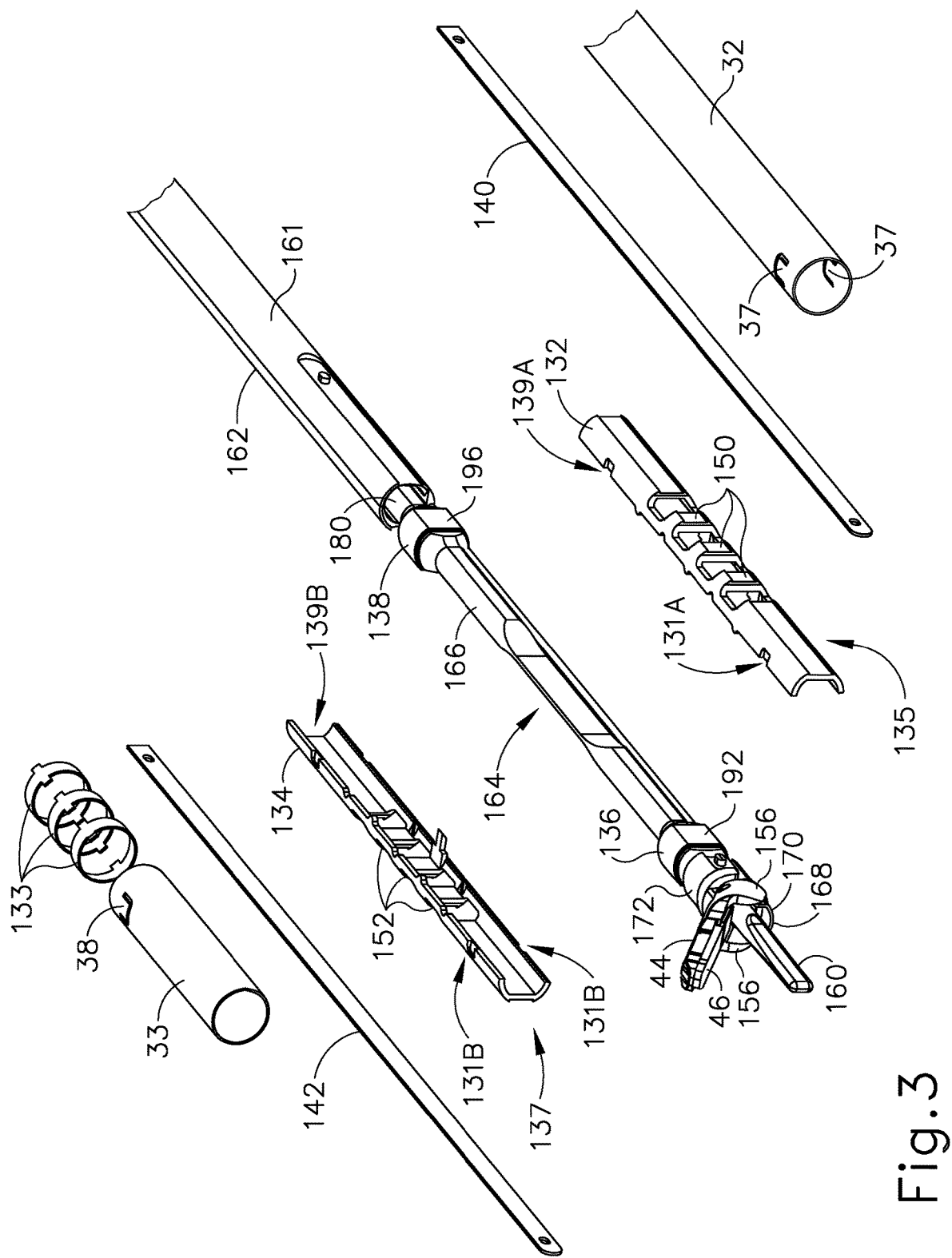
FIG. 3 depicts an exploded perspective view of the articulation section of the shaft assembly of FIG. 2.
Figure 4:
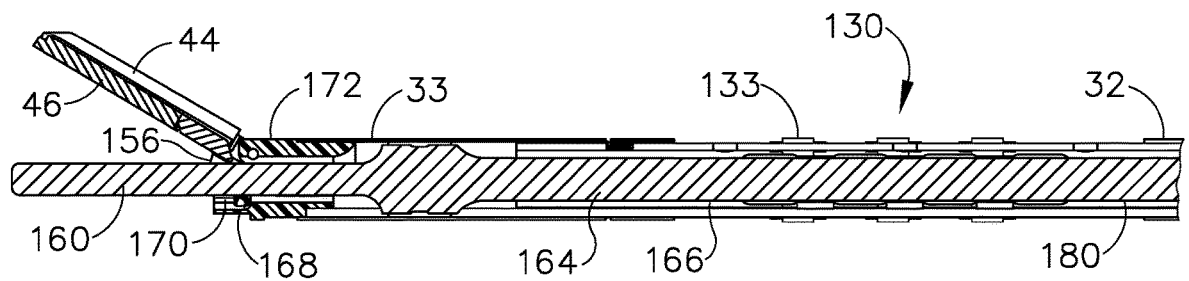
FIG. 4 depicts a cross-sectional side view of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp pad (46) may comprise polytetrafluoroethylene (PTFE) and/or any other suitable material(s). Clamp arm (44) is pivotally secured to a distally projecting tongue (43) of an upper distal shaft element (172), which is fixedly secured within a distal portion of a distal outer sheath (33). Clamp arm (44) is operable to selectively pivot toward and away from blade (160) to selectively clamp tissue between clamp arm (44) and blade (160). A pair of arms (156) extend transversely from clamp arm (44) and are pivotally secured to a lower distal shaft element (170), which is slidably disposed within the distal portion of distal outer sheath (33).

Figure 7:
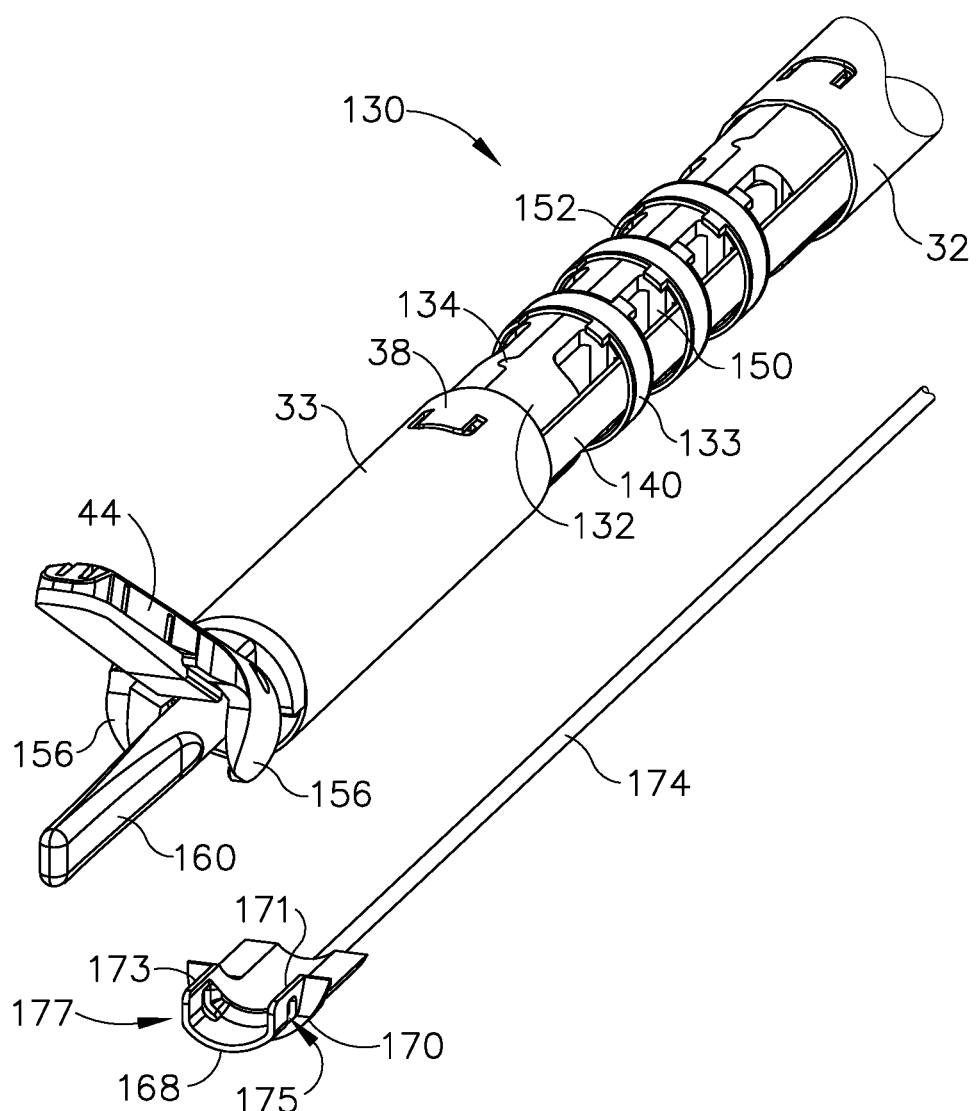
FIG. 7 depicts a partially exploded perspective view of the shaft assembly and end effector of FIG. 2.
Figure 8:
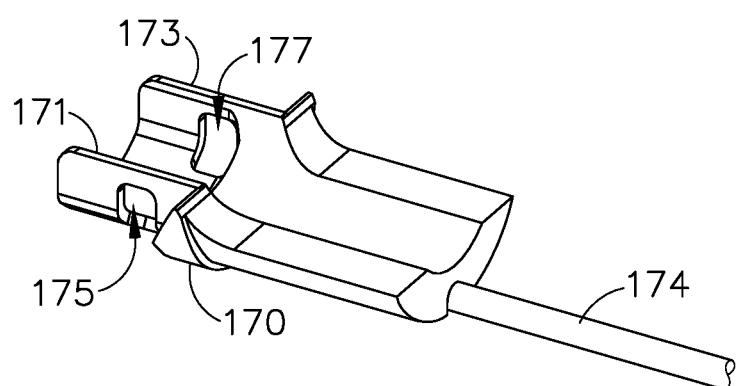
FIG. 8 depicts a perspective view of a distal collar and a drive cable of the shaft assembly of FIG. 2.

As best seen in FIGS. 7-8, a cable (174) is secured to lower distal shaft element (170). Cable (174) is operable to translate longitudinally relative to an articulation section (130) of shaft assembly (30) to selectively pivot clamp arm (44) toward and away from blade (160). In particular, cable (174) is coupled with trigger (28) such that cable (174) translates proximally in response to pivoting of trigger (28) toward pistol grip (24), and such that clamp arm (44) thereby pivots toward blade (160) in response to pivoting of trigger (28) toward pistol grip (24). In addition, cable (174) translates distally in response to pivoting of trigger (28) away from pistol grip (24), such that clamp arm (44) pivots away from blade (160) in response to pivoting of trigger (28) away from pistol grip (24).

Figure 10A:
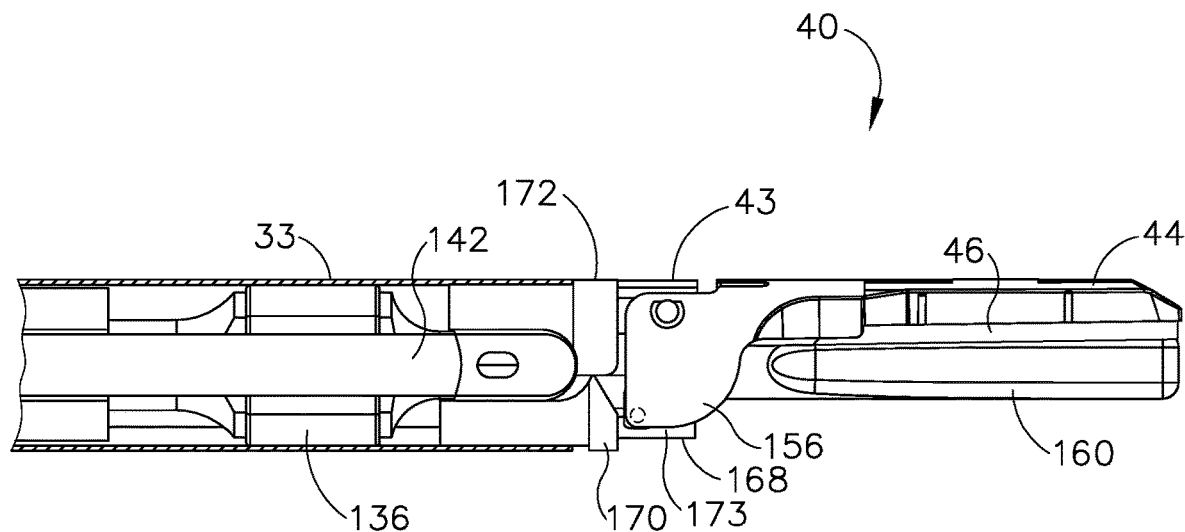
FIG. 10A depicts a side elevational view of the end effector and the distal portion of the shaft assembly of FIG. 2, with a clamp arm of the end effector in a closed position, and with an outer sheath shown in cross-section to reveal components within the outer sheath.
Figure 10B:
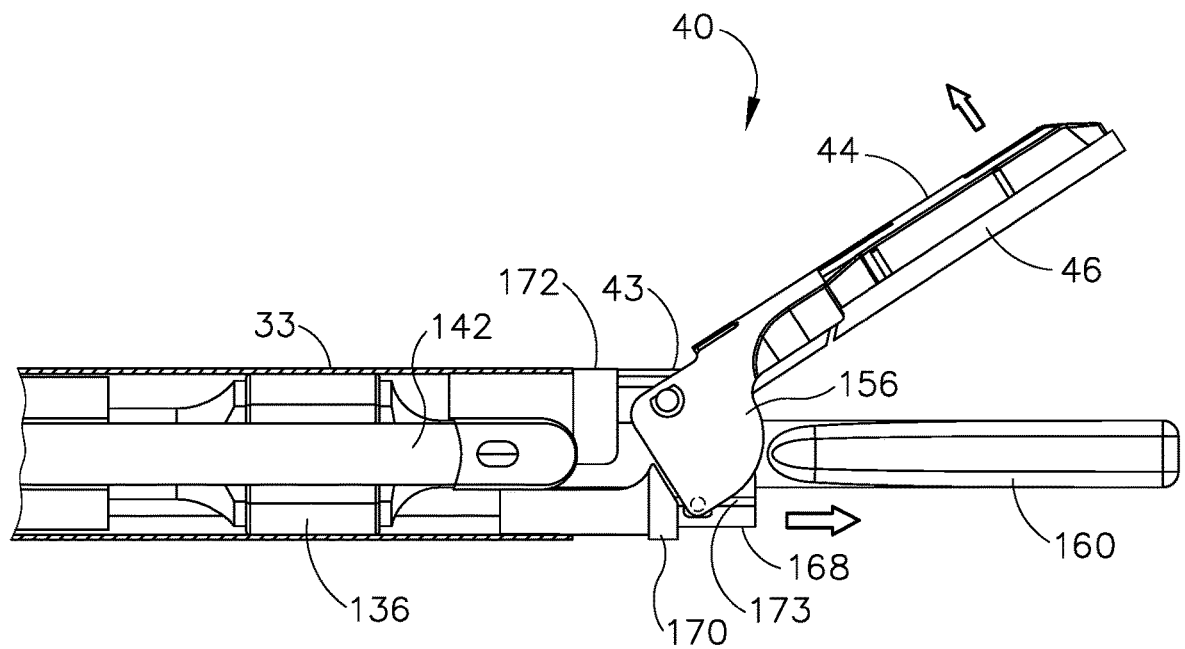
FIG. 10B depicts a side elevational view of the end effector and the distal portion of the shaft assembly of FIG. 2, with the clamp arm moved to a fully open position, and with an outer sheath shown in cross-section to reveal components within the outer sheath.

Lower distal shaft element (170) comprises a pair of distal flanges (171, 173) extending from a semi-circular base (168). Flanges (171, 173) each comprise a respective opening (175, 177). Clamp arm (44) is rotatably coupled to lower distal shaft element (170) via a pair of inwardly extending integral pins (41, 45). Pins (41, 45) extend inwardly from arms (156) of clamp arm (44) and are rotatably disposed within respective openings (175, 177) of lower distal shaft element (170). As shown in FIGS. 10A-10B, longitudinal translation of cable (174) causes longitudinal translation of lower distal shaft element (170) between a proximal position (FIG. 10A) and a distal position (FIG. 10B). Longitudinal translation of lower distal shaft element (170) causes rotation of clamp arm (44) between a closed position (FIG. 10A) and an open position (FIG. 10B).

Blade (160) of the present example is operable to vibrate at ultrasonic frequencies in order to effectively cut through and seal tissue, particularly when the tissue is being compressed between clamp pad (46) and blade (160). Blade (160) is positioned at the distal end of an acoustic drivetrain, which includes transducer assembly (12) and an acoustic waveguide (180). Acoustic waveguide (180) comprises a flexible portion (166), which is associated with articulation section (130). Transducer assembly (12) is operable to convert electrical power into ultrasonic vibrations, which are then transmitted along waveguide (180) to blade (160) in accordance with known configurations and techniques. By way of example only, this portion of the acoustic drivetrain may be configured in accordance with various teachings of various references that are cited herein.

As best seen in FIG. 3, flexible portion (166) of waveguide (180) includes a distal flange (136), a proximal flange (138), and a narrowed section (164) located between flanges (136, 138). In the present example, flanges (136, 138) are located at positions corresponding to nodes associated with resonant ultrasonic vibrations communicated through flexible portion (166) of waveguide (180) (i.e., at locations where the vibrational amplitude is minimal). Narrowed section (164) is configured to allow flexible portion (166) of waveguide (180) to flex without significantly affecting the ability of flexible portion (166) of waveguide (180) to transmit ultrasonic vibrations. By way of example only, narrowed section (164) may be configured in accordance with one or more teachings of U.S. Pub. No. 2014/0005701, now U.S. Pat. No. 9,393,037, issued on Jul. 29, 2016, and/or U.S. Pub. No. 2014/0114334, now U.S. Pat. No. 9,095,367, issued on Aug. 4, 2015, the disclosures of which are incorporated by reference herein. Various suitable ways in which waveguide (180) may be mechanically and acoustically coupled with transducer assembly (12) will be apparent to those of ordinary skill in the art in view of the teachings herein.

Those of ordinary skill in the art will understand that, as a matter of physics, the distal end of blade (24) is located at a position corresponding to an anti-node associated with resonant ultrasonic vibrations communicated through waveguide (28) (i.e., at an acoustic anti-node). When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When tissue is compressed between blade (160) and clamp pad (46), the ultrasonic oscillation of blade (160) may simultaneously sever the tissue and denature the proteins in adjacent tissue cells, thereby providing a coagulative effect with relatively little thermal spread.

In some versions, end effector (40) is operable to apply radiofrequency (RF) electrosurgical energy to tissue in addition to applying ultrasonic energy to tissue. By way of example only, end effector (40) may be configured and operable in accordance with at least some of the teachings of U.S. Pub. No. 2015/0141981, entitled "Ultrasonic Surgical Instrument with Electrosurgical Feature," published May 21, 2015, now U.S. Pat. No. 9,949,785, issued on Apr. 24, 2018, the disclosure of which is incorporated by reference herein; and/or U.S. Pat. No. 8,663,220, entitled "Ultrasonic Electrosurgical Instruments," issued Mar. 4, 2014, the disclosure of which is incorporated by reference herein. Other suitable configurations for an acoustic transmission assembly and transducer assembly (12) will be apparent to one of ordinary skill in the art in view of the teachings herein. Similarly, other suitable configurations for end effector (40) will be apparent to those of ordinary skill in the art in view of the teachings herein.

B. Exemplary Shaft Assembly and Articulation Section

Shaft assembly (30) of the present example extends distally from handle assembly (20). As shown in FIGS. 2-7, shaft assembly (30) includes distal outer sheath (33) and a proximal outer sheath (32) that enclose clamp arm (44) drive features and the above-described acoustic transmission features. Shaft assembly (30) further includes an articulation section (130), which is located at a distal portion of shaft assembly (30), with end effector (40) being located distal to articulation section (130). As shown in FIG. 1, a rotation control assembly (102) has rotation control member in the form of rotation control knob (31), which is secured to a proximal portion of proximal outer sheath (32). Knob (31) is rotatable relative to body (22), such that shaft assembly (30) is rotatable about the longitudinal axis defined by outer sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to a longitudinal axis defined by outer sheath (32). Articulation section (130) may take a variety of forms. By way of example only, articulation section (130) may be configured in accordance with one or more teachings of U.S. Pub. No. 2012/0078247, now U.S. Pat. No. 9,402,682, issued on Aug. 2, 2016, the disclosure of which is incorporated by reference herein. As another merely illustrative example, articulation section (130) may be configured in accordance with one or more teachings of U.S. Pub. No. 2014/0005701, now U.S. Pat. No. 9,393,037, issued on Jul. 29, 2016, and/or U.S. Pub. No. 2014/0114334, now U.S. Pat. No. 9,095,367, issued on Aug. 4, 2015, the disclosures of which are incorporated by reference herein. Various other suitable forms that articulation section (130) may take will be apparent to those of ordinary skill in the art in view of the teachings herein.

As best seen in FIGS. 2-6B articulation section (130) of this example comprises a set of three retention collars (133) and a pair of ribbed body portions (132, 134), with a pair of articulation bands (140, 142) extending along respective channels (135, 137) defined between interior surfaces of retention collars (133) and exterior surfaces of ribbed body portions (132, 134). Ribbed body portions (132, 134) are longitudinally positioned between flanges (136, 138) of flexible portion (166) of waveguide (180). Ribbed body portions (132, 134) are configured to flex with flexible portion (166) of waveguide (180) when articulation section (130) bends to achieve an articulated state.

FIG. 3 shows ribbed body portions (132, 134) in greater detail. Ribbed body portion (132) comprises a set of three ribs (150) that are configured to promote lateral flexing of ribbed body portion (132). Ribbed body portion (132) also defines a channel (135) that is configured to receive articulation band (140) while allowing articulation band (140) to slide relative to ribbed body portion (132). Similarly, ribbed body portion (134) comprises a set of three ribs (152) that are configured to promote lateral flexing of ribbed body portion (134). Of course, any other suitable number of ribs (150, 152) may be provided. Ribbed body portion (134) also defines a channel (137) that is configured to receive articulation band (142) while allowing articulation band (142) to slide relative to ribbed body portion (137).

Figure 5:
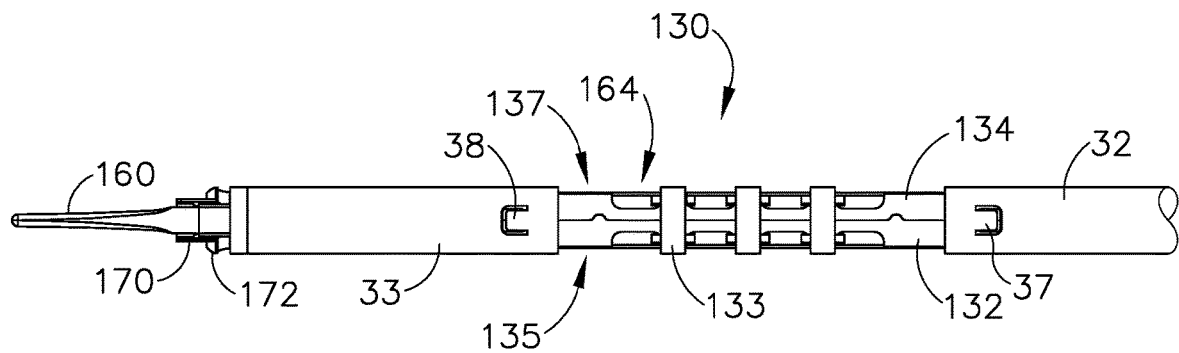
FIG. 5 depicts a top plan view of the shaft assembly and end effector of FIG. 2.

As best seen in FIG. 5, ribbed body portions (132, 134) are laterally interposed between articulation bands (140, 142) and flexible portion (166) of waveguide (180). Ribbed body portions (132, 134) mate with each other such that they together define an internal passage sized to accommodate flexible portion (166) of waveguide (180) without contacting waveguide (180). In addition, when ribbed body portions (132, 134) are coupled together, a pair of complementary distal notches (131A, 131B) formed in ribbed body portions (132, 134) align to receive a pair of inwardly projecting resilient tabs (38) of distal outer sheath (33). This engagement between tabs (38) and notches (131A, 131B) longitudinally secures ribbed body portions (132, 134) relative to distal outer sheath (33). Similarly, when ribbed body portions (132, 134) are coupled together, a pair of complementary proximal notches (139A, 139B) formed in ribbed body portions (132, 134) align to receive a pair of inwardly projecting resilient tabs (37) of proximal outer sheath (32). This engagement between tabs (37) and notches (139A, 139B) longitudinally secures ribbed body portions (132, 134) relative to proximal outer sheath (32). Of course, any other suitable kinds of features may be used to couple ribbed body portions (132, 134) with proximal outer sheath (32) and/or distal outer sheath (33).

Figure 6A:
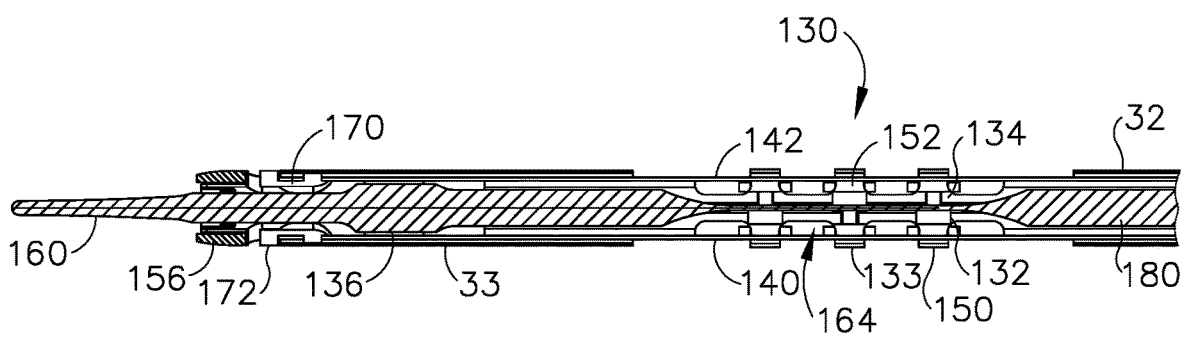
FIG. 6A depicts a cross-sectional top view of the shaft assembly and end effector of FIG. 2 in a straight configuration.
Figure 6B:
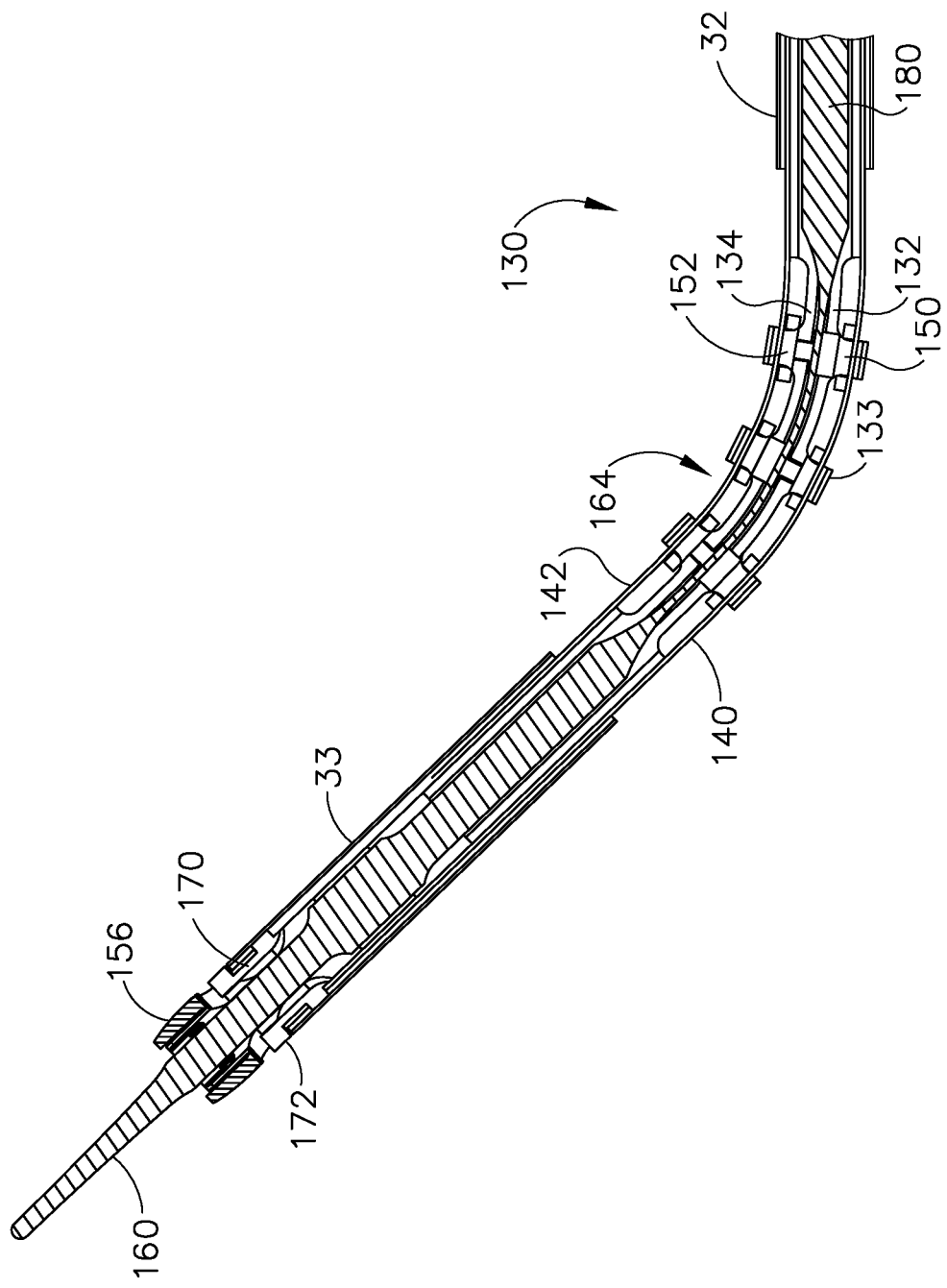
FIG. 6B depicts a cross-sectional top view of the shaft assembly and end effector of FIG. 2 in an articulated configuration.

The distal ends of articulation bands (140, 142) are unitarily secured to upper distal shaft element (172). When articulation bands (140, 142) translate longitudinally in an opposing fashion, this will cause articulation section (130) to bend, thereby laterally deflecting end effector (40) away from the longitudinal axis of shaft assembly (30) from a straight configuration as shown in FIG. 6A to an articulated configuration as shown in FIG. 6B. In particular, end effector (40) will be articulated toward the articulation band (140, 142) that is being pulled proximally. During such articulation, the other articulation band (140, 142) may be pulled distally by upper distal shaft element (172). Alternatively, the other articulation band (140, 142) may be driven distally by an articulation control. Ribbed body portions (132, 134) and narrowed section (164) are all sufficiently flexible to accommodate the above-described articulation of end effector (40). Furthermore, flexible acoustic waveguide (166) is configured to effectively communicate ultrasonic vibrations from waveguide (180) to blade (160) even when articulation section (130) is in an articulated state as shown in FIG. 6B.

As best seen in FIG. 3, each flange (136, 138) of waveguide (180) includes a respective pair of opposing flats (192, 196). Flats (192, 196) are oriented along vertical planes that are parallel to a vertical plane extending through narrowed section (164) of flexible portion (166). Flats (192, 196) are configured to provide clearance for articulation bands (140, 142). In particular, flats (196) of proximal flange (138) accommodate articulation bands (140, 142) between proximal flange (138) and the inner diameter of proximal outer sheath (32); while flats (192) of distal flange (136) accommodate articulation bands (140, 142) between distal flange (136) and the inner diameter of distal outer sheath (33). Of course, flats (192, 196) could be substituted with a variety of features, including but not limited to slots, channels, etc., with any suitable kind of profile (e.g., square, flat, round, etc.). It should also be understood that waveguide (180) may include flats formed in accordance with at least some of the teachings of U.S. Pub. No. 2013/0289592, entitled "Ultrasonic Device for Cutting and Coagulating," filed Apr. 23, 2013, published on Oct. 31, 2013, now U.S. Pat. No. 10,238,416, issued on Mar. 26, 2019, the disclosure of which is incorporated by reference herein.

In the present example, outer rings (133) are located at longitudinal positions corresponding to ribs (150, 152), such that three rings (133) are provided for three ribs (150, 152). Articulation band (140) is laterally interposed within channel (135) between rings (133) and ribbed body portion (132); while articulation band (142) is laterally interposed within channel (137) between rings (133) and ribbed body portion (134). Rings (133) are configured to keep articulation bands (140, 142) in a parallel relationship, particularly when articulation section (130) is in a bent configuration (e.g., similar to the configuration shown in FIG. 6B). In other words, when articulation band (140) is on the inner diameter of a curved configuration presented by a bent articulation section (130), rings (133) may retain articulation band (140) such that articulation band (140) follows a curved path that complements the curved path followed by articulation band (142). It should be understood that channels (135, 137) are sized to accommodate respective articulation bands (140, 142) in such a way that articulation bands (140, 142) may still freely slide through articulation section (130), even with rings (133) being secured to ribbed body portions (150, 152). It should also be understood that rings (133) may be secured to ribbed body portions (132, 134) in various ways, including but not limited to interference fitting, adhesives, welding, etc.

When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180).

As best seen in FIG. 9, an articulation control assembly (100) is secured to a proximal portion of outer sheath (32). Articulation control assembly (100) comprises a housing (110) and a rotatable articulation control knob (120). As shown and described herein, articulation control assembly (100) and rotation control assembly (102) collectively define a shaft control assembly (98). Housing (110) comprises a pair of perpendicularly intersecting cylindrical portions (112, 114). Knob (120) is rotatably disposed within a first hollow cylindrical portion (112) of housing (110) such that knob (120) is operable to rotate within cylindrical portion (112) of housing (110). Shaft assembly (30) is slidably and rotatably disposed within a second hollow cylindrical portion (114). Shaft assembly (30) comprises a pair of translatable members (161, 162), both of which extend slidably and longitudinally through the proximal portion of outer sheath (32). Translatable members (161, 162) are longitudinally translatable within second cylindrical portion (114) between a distal position and a proximal position. Translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142).

Knob (120) comprises a pair of pins (122, 124) extending downwardly from a bottom surface of knob (120). Pins (122, 124) extend into second cylindrical portion (114) of housing (110) and are rotatably and slidably disposed within a respective pair of channels (163A, 163B) formed in top surfaces of translatable members (161, 162). Channels (163A, 163B) are positioned on opposite sides of an axis of rotation of knob (120), such that rotation of knob (120) about that axis causes opposing longitudinal translation of translatable members (161, 162). For instance, rotation of knob (120) in a first direction causes distal longitudinal translation of translatable member (161) and articulation band (140), and proximal longitudinal translation of translatable member (162) and articulation band (142); and rotation of knob (120) in a second direction causes proximal longitudinal translation of translatable member (161) and articulation band (140), and distal longitudinal translation of translatable member (162) and articulation band (142). Thus, it should be understood that rotation of rotation knob (120) causes articulation of articulation section (130).

Housing (110) of articulation control assembly (100) comprises a pair of set screws (111, 113) extending inwardly from an interior surface of first cylindrical portion (112). With knob (120) rotatably disposed within first cylindrical portion (112) of housing (110), set screws (111, 113) are slidably disposed within a pair of arcuate channels (121, 123) formed in knob (120). Thus, it should be understood that rotation of knob (120) will be limited by movement of set screws (111, 113) within channels (121, 123). Set screws (111, 113) also retain knob (120) in housing (110), preventing knob (120) from traveling vertically within first cylindrical portion (112) of housing (110).

An interior surface of first cylindrical portion (112) of housing (110) comprises a first angular array of teeth (116) and a second angular array of teeth (118) formed in an interior surface of first cylindrical portion (112). Rotation knob (120) comprises a pair of outwardly extending engagement members (126, 128) that are configured to engage teeth (116, 118) of first cylindrical portion (112) in a detent relationship to thereby selectively lock knob (120) in a particular rotational position. The engagement of engagement members (126, 128) with teeth (116, 118) may be overcome by a user applying sufficient rotational force to knob (120); but absent such force, the engagement will suffice to maintain the straight or articulated configuration of articulation section (130). It should therefore be understood that the ability to selectively lock knob (120) in a particular rotational position lock will enable an operator to selectively lock articulation section (130) in a particular deflected position relative to the longitudinal axis defined by outer sheath (32).

In some versions of instrument (10), articulation section (130) of shaft assembly (30) is operable to achieve articulation angles up to between approximately 15° and approximately 30°, both relative to the longitudinal axis of shaft assembly (30) when shaft assembly (30) is in a straight (non-articulated) configuration. Alternatively, articulation section (130) may be operable to achieve any other suitable articulation angles.

II. Exemplary Shaft Control Assembly with Dual Mode Articulation Control Assembly It may be desirable to provide a dual mode articulation control assembly that is operable to drive articulation of articulation section (130) with various input sensitivities. In some instances, an operator may wish to rapidly provide a relative large degree of articulation of articulation section (130) with relatively little input sensitivity (e.g., less accuracy and/or less precision for positioning end effector (40)). In some other instances, an operator may wish to provide a finer adjustment of articulation with relatively greater input sensitivity (e.g., more accuracy and/or more precision for positioning end effector (40)). The following description relates to an exemplary ultrasonic surgical instrument (210) having a dual mode articulation control assembly (218) that includes at least two articulation control members (222, 223) with differing high and low transmission ratios for improved articulation control of shaft assembly (216). Aside from the differences described below, instrument (210) of this example is configured and operable just like instrument (10) described above.

Figure 11:
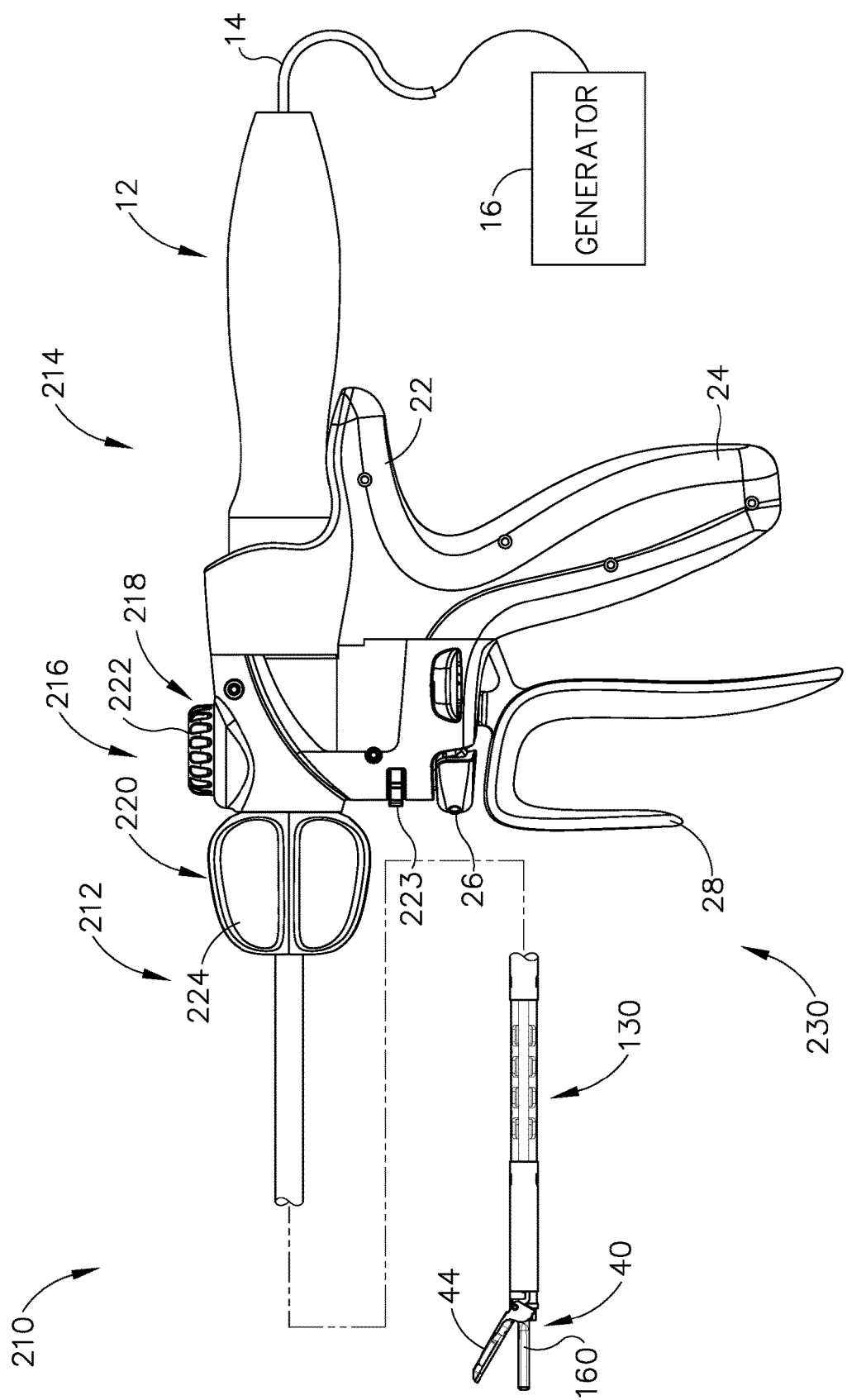
FIG. 11 depicts a side elevational view of a second exemplary ultrasonic surgical instrument having a shaft control assembly.
Figure 12:
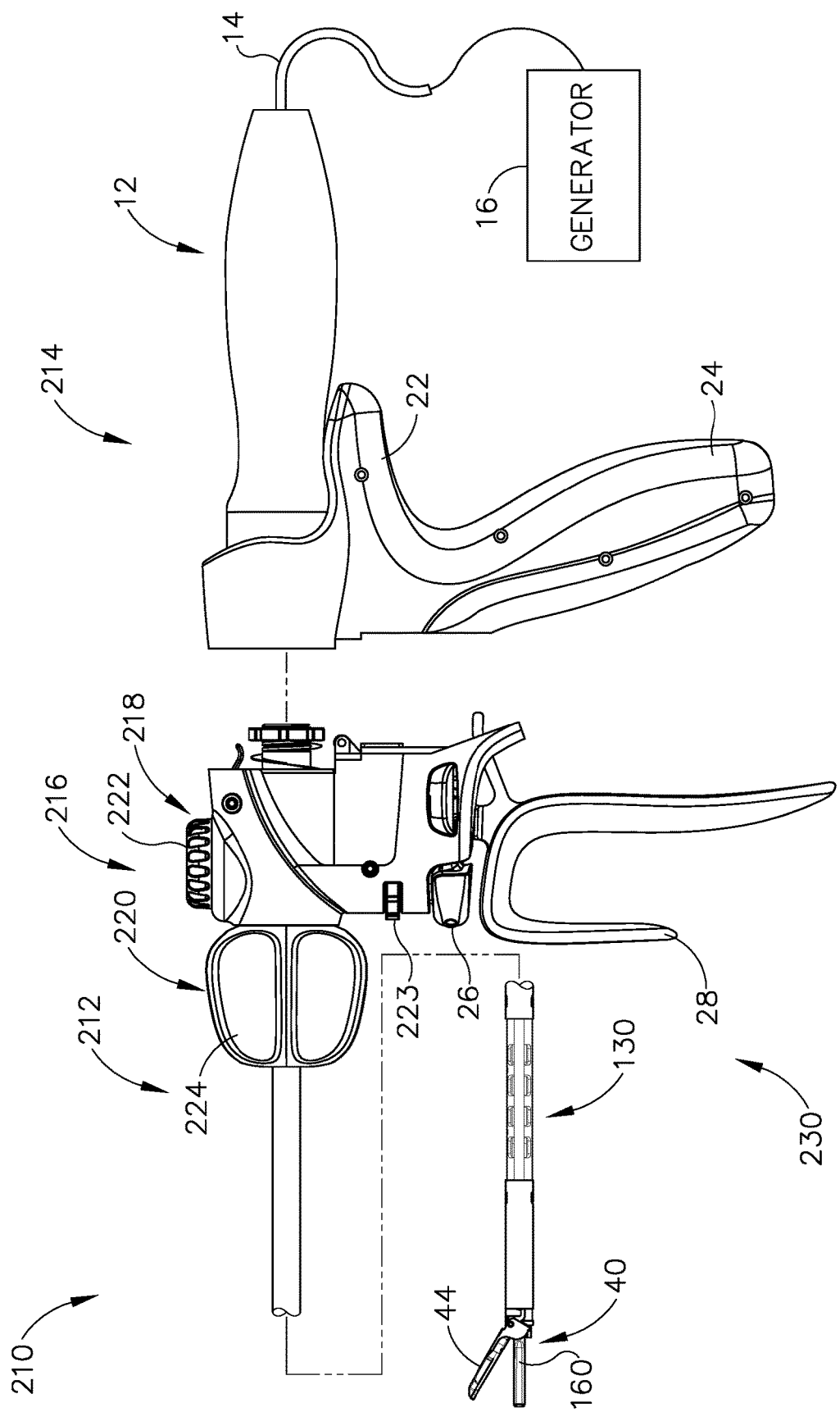
FIG. 12 depicts a partially exploded side elevation view of the ultrasonic surgical instrument of FIG. 11, with a disposable assembly separated from a reusable assembly.

As shown in FIGS. 11-12, instrument (210) of the present example further includes a shaft assembly (212), a handle assembly (214), end effector (40), and acoustic waveguide (80) extending therealong. As discussed above, acoustic waveguide (80) is operatively connected to generator (16) and shaft assembly (212), which includes articulation section (130) for positioning end effector (40) during a surgical procedure. To this end, surgical instrument (210) includes a shaft control assembly (216) that is configured to rotate shaft assembly (212) about the longitudinal axis and articulate articulation section (130). Shaft control assembly (216) more particularly includes an articulation control assembly (218) that is operatively connected to the articulation section (130); and a rotation control assembly (220) that is operatively connected to shaft assembly (212). Articulation control assembly (218) includes a high articulation control member (222) and a low articulation control member (223). Rotation control assembly includes a rotation control member (224). Articulation control assembly (218) further includes a transmission assembly (226) with a high ratio drive (227) (see FIG. 14) and a low ratio drive (228) (see FIG. 14) configured to respectively transmit selective manipulation of high and low articulation control members (222, 223) to shaft assembly (212) for flexing articulation section (130) with two distinct input sensitivities.

A distal portion of shaft control assembly (216) extends along a proximal portion of shaft assembly (212). A proximal portion of shaft control assembly (216) is contained within a disposable assembly (230) of surgical instrument (210). Disposable assembly (230) is configured to removably connect with handle assembly (214) to form surgical instrument (210). By way of example only, handle assembly (214) may be configured and operable in accordance with at least some of the teachings of U.S. patent application Ser. No. 14/868,574, entitled "Ultrasonic Surgical Instrument with Removable Handle Assembly," filed on Sep. 25, 2015, now published as U.S. Pat. Pub. No. 2016/0015419, published on Jan. 21, 2016, the disclosure of which is hereby incorporated by reference in its entirety. By way of further example only, assemblies (214, 230) may couple together (and decouple from each other) in accordance with at least some of the teachings of U.S. patent application Ser. No. 14/868,574, entitled "Ultrasonic Surgical Instrument with Removable Handle Assembly," filed on Sep. 25, 2015, now published as U.S. Pat. Pub. No. 2016/0015419, published on Jan. 21, 2016, the disclosure of which is hereby incorporated by reference in its entirety. Alternatively, assemblies (214, 230) may couple together (and decouple from each other) in any other suitable fashion. In some other versions, instrument (210) is constructed without separable assemblies (214, 230). For instance, instrument (210) may instead be constructed just like instrument (10), but with articulation control assembly (218) replacing articulation control assembly (100).

Figure 13:
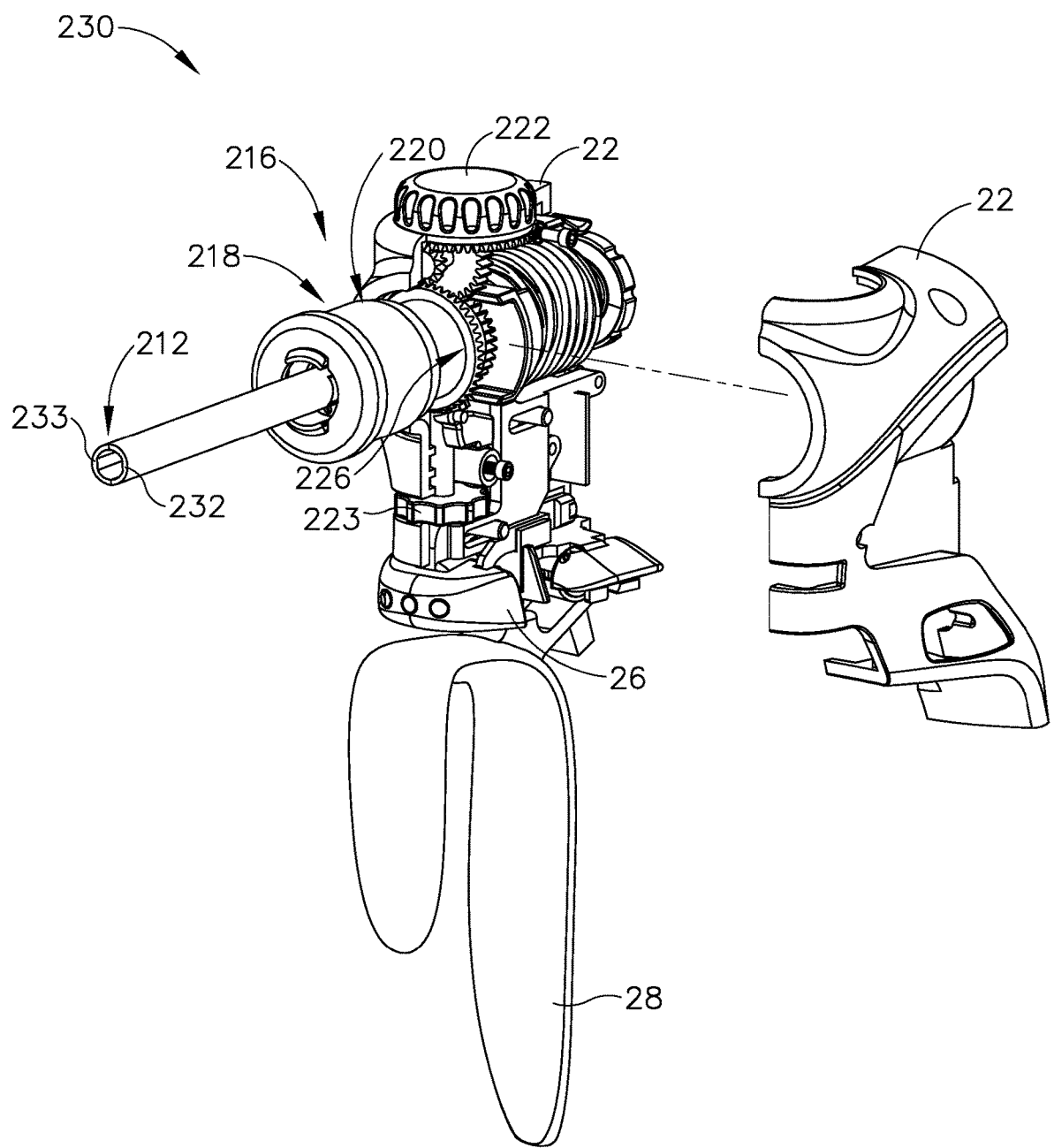
FIG. 13 depicts a partially exploded front perspective view of the disposable assembly of FIG. 12, which includes a shaft control assembly having a dual mode articulation control assembly.

As shown in FIG. 13, a lateral side portion of disposable assembly (230) is removed to more clearly illustrate the proximal portion of shaft control assembly (216). In one example, rotation and high and low articulation control members (224, 222, 223) are respectively in the form of a selectively rotatable rotation control knob (224) and selectively rotatable high and low articulation control knobs (222, 223). Rotation control knob (220) extends along the longitudinal axis of shaft assembly (212) and is configured to rotate about the longitudinal axis. In contrast, high articulation control knob (222) extends along a high transverse axis and is configured to rotate about the high transverse axis; while low articulation control knob (223) extends along a low transverse axis and is configured to rotate about the low transverse axis. Thus, rotation control knob (224) rotates perpendicularly relative to high and low articulation control knobs (222, 223). Rotation and low articulation control knobs (223, 224) are each also positioned proximate to trigger (28) of handle assembly (214) such that the operator can access and manipulate trigger (28), rotation control knob (224), and low articulation control knob (223) with the same single hand that grasps pistol grip (24).

In the present example, low articulation control knob (223) is received within a knob slot (231) (see FIG. 30), transversely positioned between rotation control knob (224) and trigger (28). High articulation control knob (222) extends from an upper surface of housing (22). While the above description positions exemplary shaft control assembly (216) at least partially within handle assembly (214) with the positions of the rotation and low articulation control knobs (224, 223) proximate to trigger (28), it will be appreciated that one or more portions of shaft control assembly (216) may be alternatively positioned for operative connection with shaft assembly (212). Thus, the invention is not intended to be unnecessarily limited to the specific orientation and placement of the shaft control assembly (216) as described herein.

Figure 14:
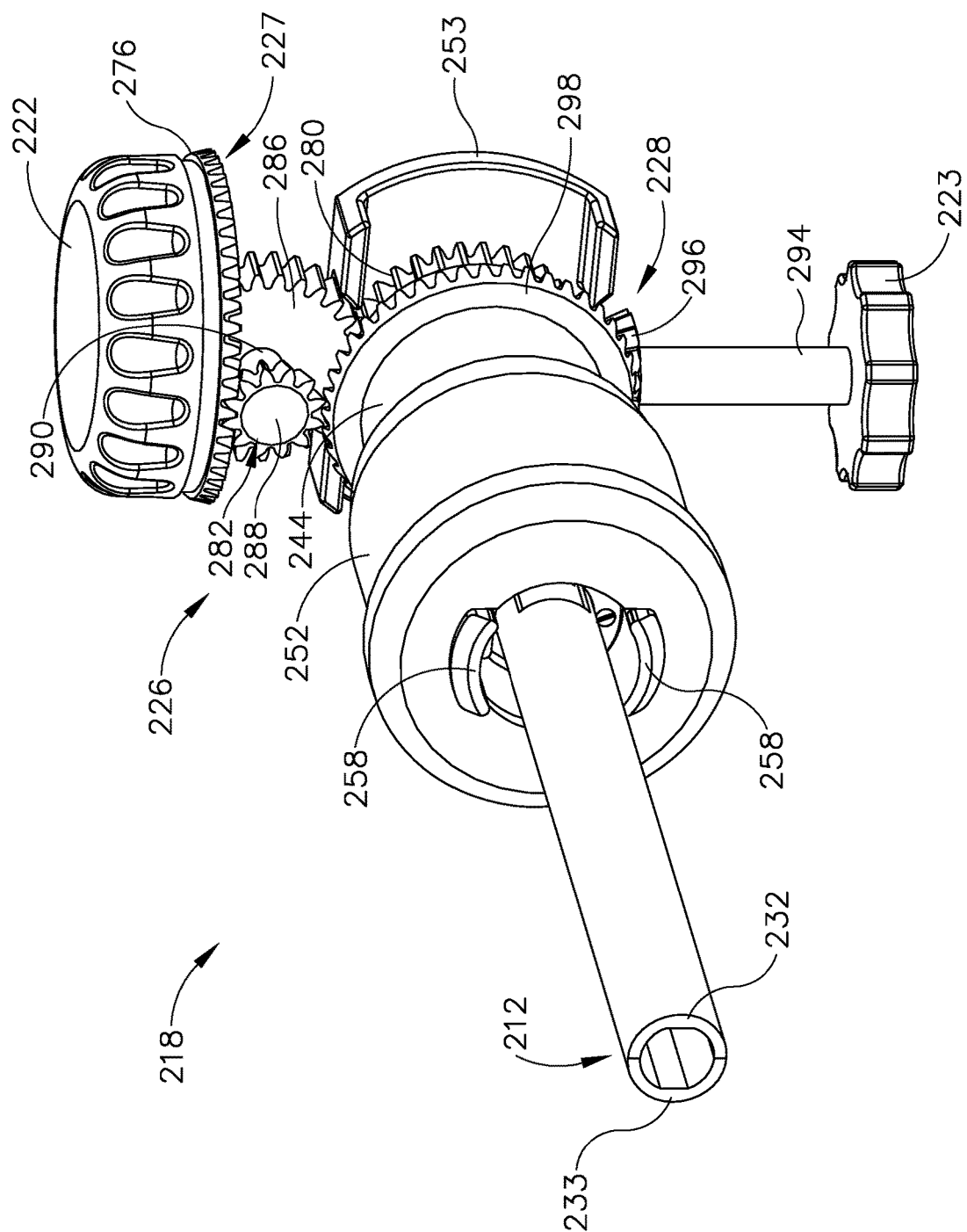
FIG. 14 depicts a front perspective view of the dual mode articulation control assembly of FIG. 13.
Figure 15:
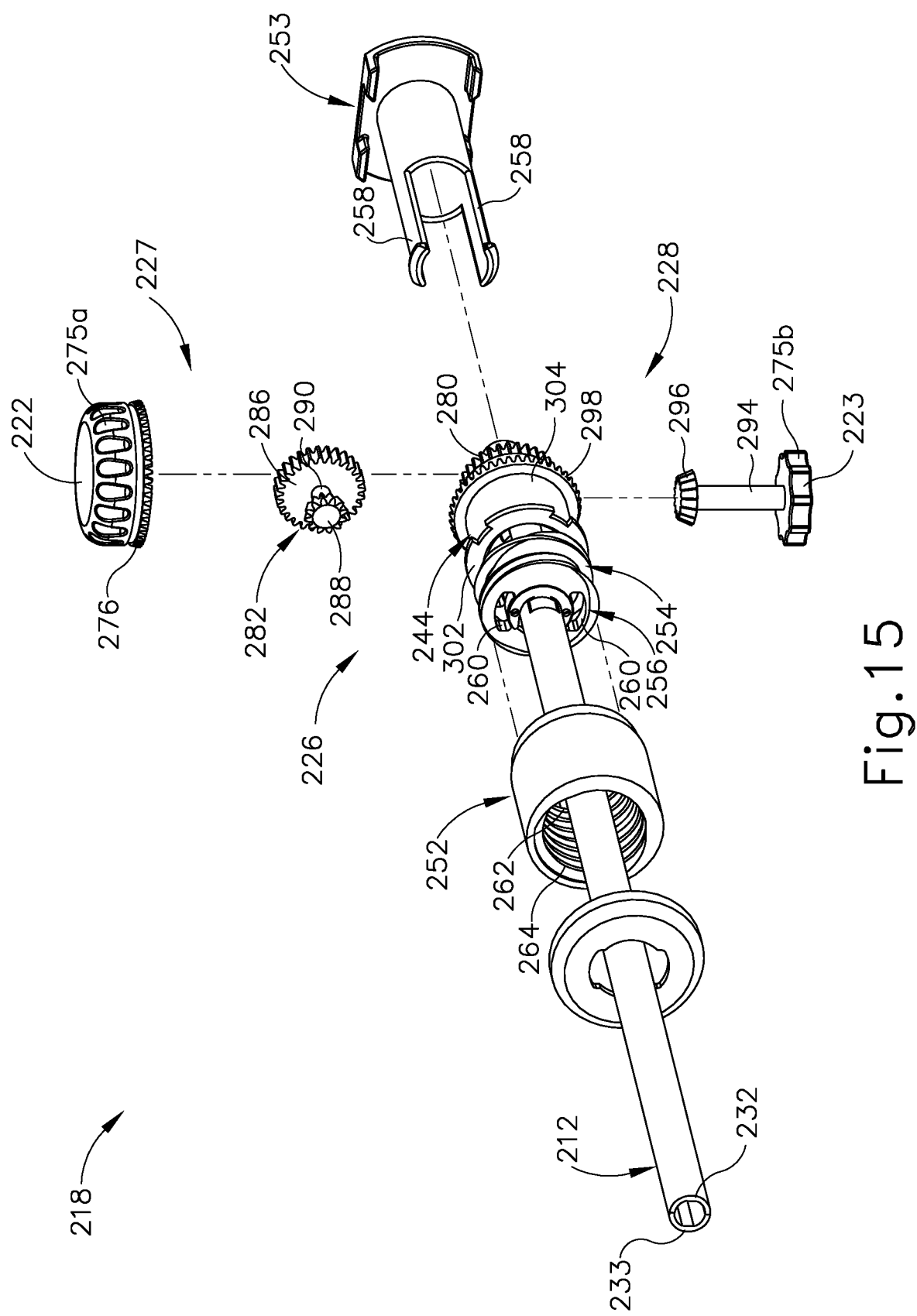
FIG. 15 depicts a partially exploded front perspective view of the dual mode articulation control assembly of FIG. 13.

FIGS. 14-15 illustrate shaft control assembly (216) and a pair of translatable members (232, 233), which extend to respective articulation bands (140, 142) for directing articulation along shaft assembly (216) as discussed above with respect to shaft assembly (30) (see FIG. 3). Translatable members (232, 233) differ from translatable members (161, 162) by at least having a pair of longitudinal slots (234, 236) that extend laterally through translatable members (232, 233) to respectively receive pins (not shown). Pins (not shown) extend through rotation control knob (224) such that pins (not shown) secure rotation control knob (224) to translatable members (232, 233). Thus, as the operator selectively rotates rotation control knob (224) about the longitudinal axis of shaft assembly (212), rotation control knob (224) causes rotation of translatable members (232, 233) and the other portions of shaft assembly (212) about the longitudinal axis as discussed above with respect to surgical instrument (10) (see FIG. 1). Additional components of rotation control assembly (220) will be discussed below in further detail.

Transmission assembly (226) is configured to transmit selective movement, such as rotational input by the operator via high and low articulation control knobs (222, 223), to shaft assembly (212) for articulating articulation section (130) (see FIG. 11). Transmission assembly (226) includes a drive drum (244), a high ratio drive (227) connected to high articulation control member, and a low ratio drive (228) connected to low articulation control member (223). High and low ratio drives (227, 228) are each connected to drive drum (244) for transmitting manipulation therethrough as discussed below in greater detail. A distal end of drive drum (244) rigidly connects to a proximal end of an articulation drum (252) such that each surrounds and is configured to rotate about the longitudinal axis for directing articulation of articulation section (130) (see FIG. 11).

Figure 16:
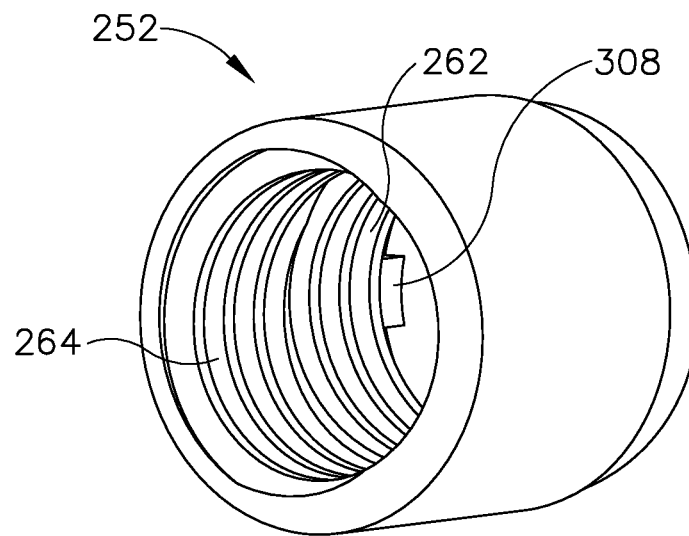
FIG. 16 depicts an front perspective view of an articulation drum of the dual mode articulation control assembly of FIG. 13.
Figure 17:
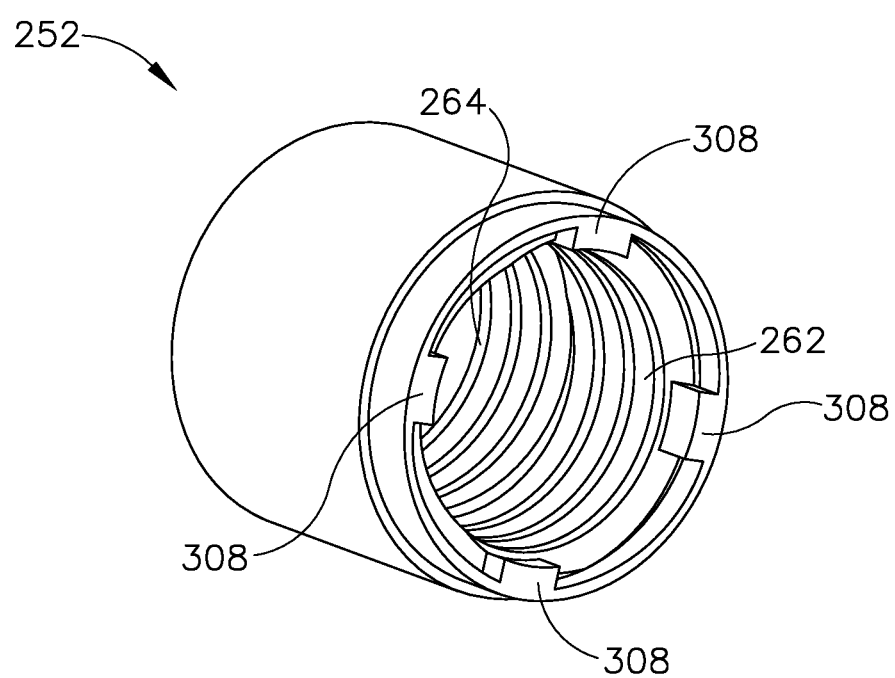
FIG. 17 depicts a rear perspective view of the articulation drum of FIG. 16.

To this end, with respect to FIGS. 15-17, articulation control assembly (216) further includes a frame (253), a proximal lead screw (254), and a distal lead screw (256) received within articulation drum (252) for converting rotation of articulation drum (252) to linear movement of lead screws (254, 256) to thereby articulate articulation section (130) (see FIG. 11). In the present example, frame (253) had a pair of generally parallel and offset longitudinal tracks (258) received within respective recesses (260). Tracks (258) are configured to prevent rotation of proximal and distal lead screws (254, 256) while allowing for translation of lead screws (254, 256) along the longitudinal axis. Rotation of articulation drum (216) is configured to cause translation of lead screws (254, 256). More particularly, proximal lead screw (254) threadably engages proximal inner threads (262), while distal lead screw (256) threadably engages distal inner threads (264). Proximal and distal inner threads (262, 264) have opposing pitches relative to each other such that rotation of drum (252) results in translation of proximal and distal lead screws (254, 256) in opposing directions.

Figure 18:
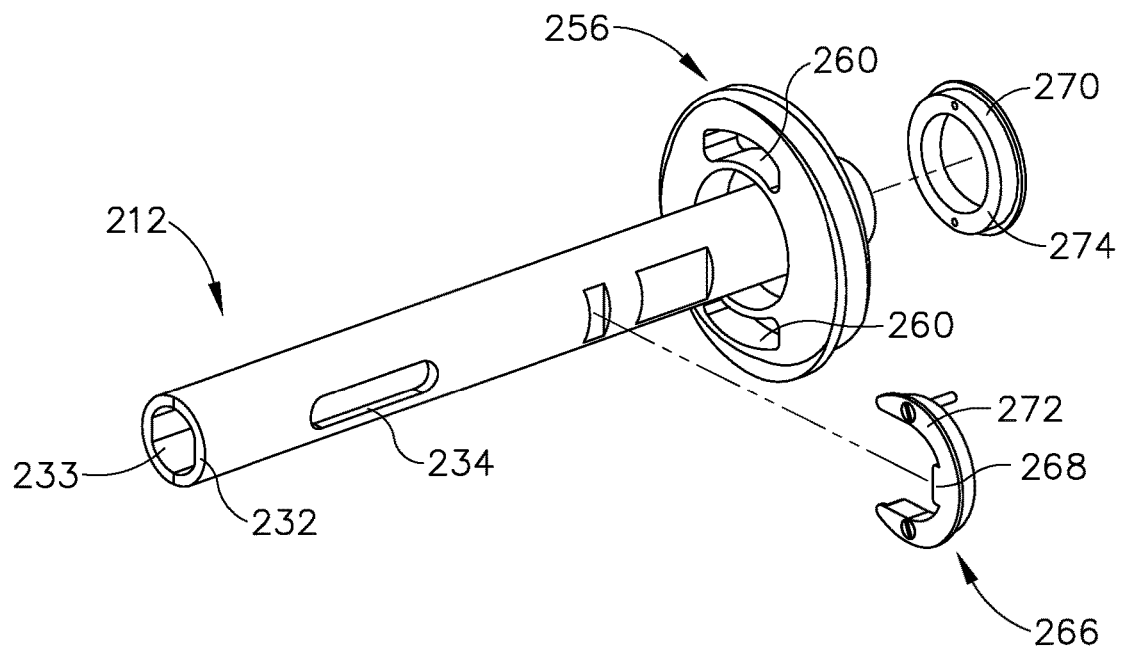
FIG. 18 depicts an exploded front perspective view of a lead screw of the dual mode articulation control assembly of FIG. 13.
Figure 19:
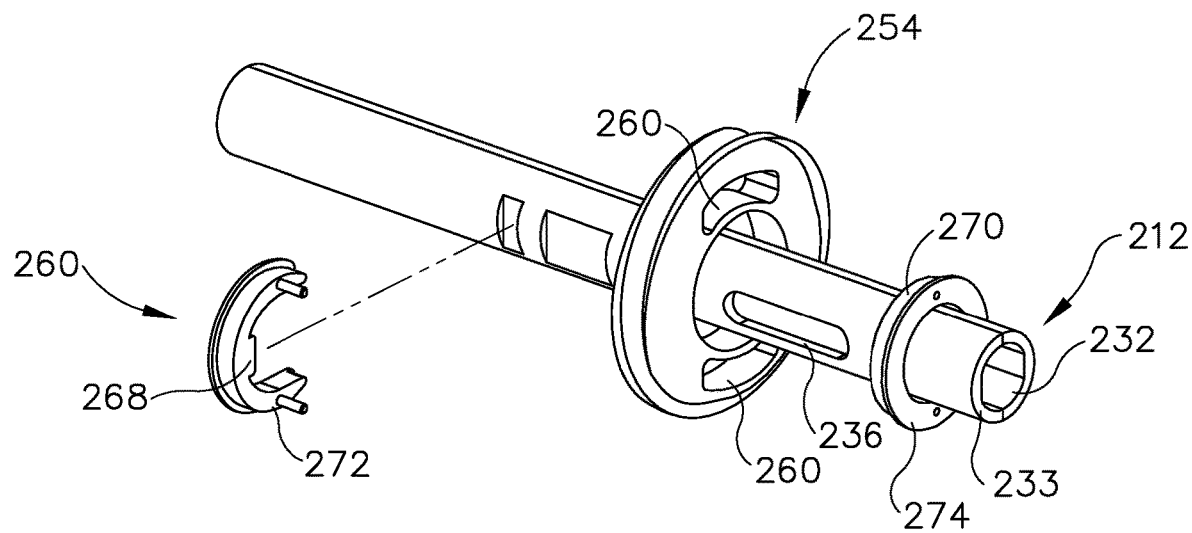
FIG. 19 depicts an exploded rear perspective view of another lead screw of the dual mode articulation control assembly of FIG. 13.
Figure 22:
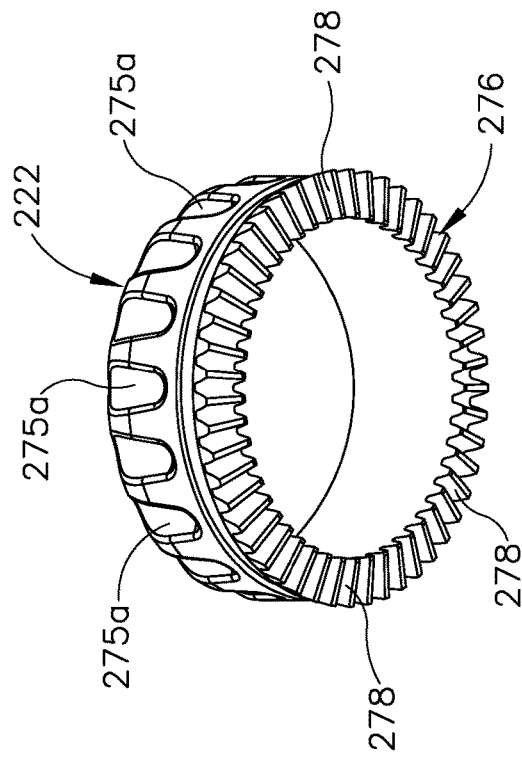
FIG. 22 depicts an upper perspective view of a low sensitivity articulation control knob of the dual sensitivity drive of FIG. 20.
Figure 23:
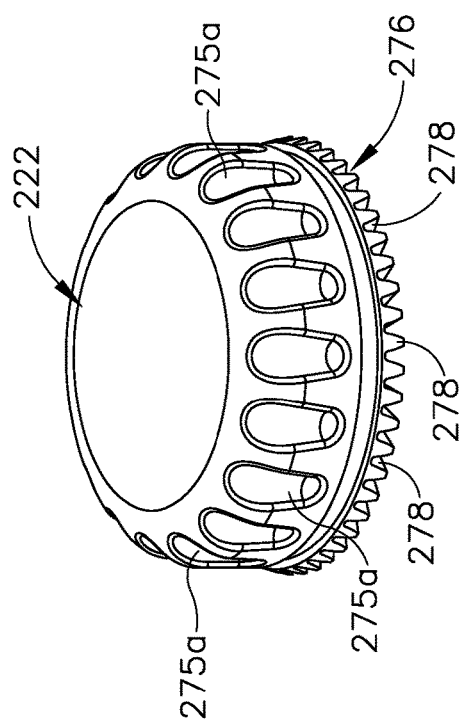
FIG. 23 depicts a lower perspective view of the low sensitivity articulation control knob of FIG. 22.
Figure 24:
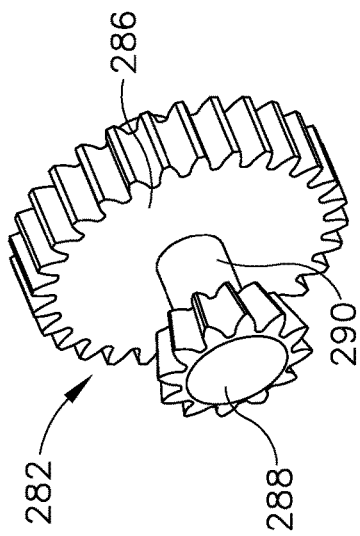
FIG. 24 depicts a rear perspective view of a drive coupling of the dual sensitivity drive of FIG. 20.
Figure 25:
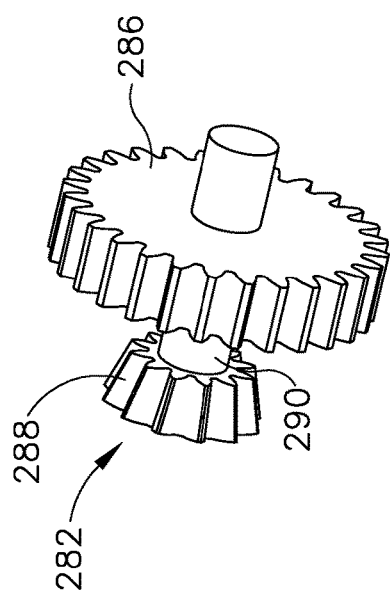
FIG. 25 depicts a front perspective view of the drive coupling of FIG. 24.
Figure 27:
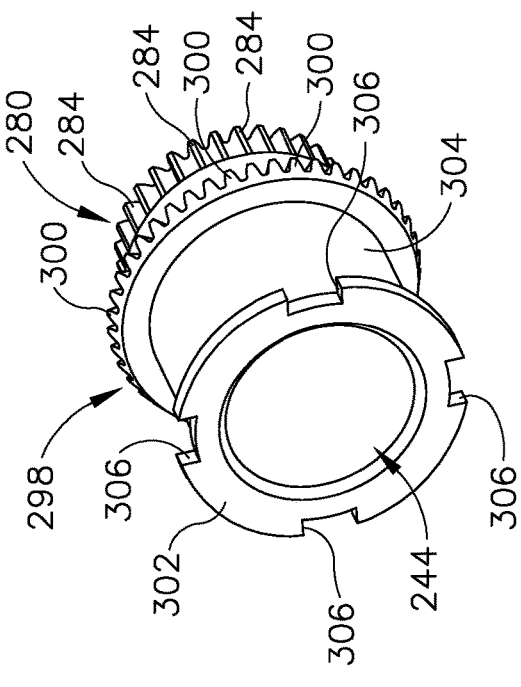
FIG. 27 depicts a front perspective view of the drive drum of FIG. 26.
Figure 26:
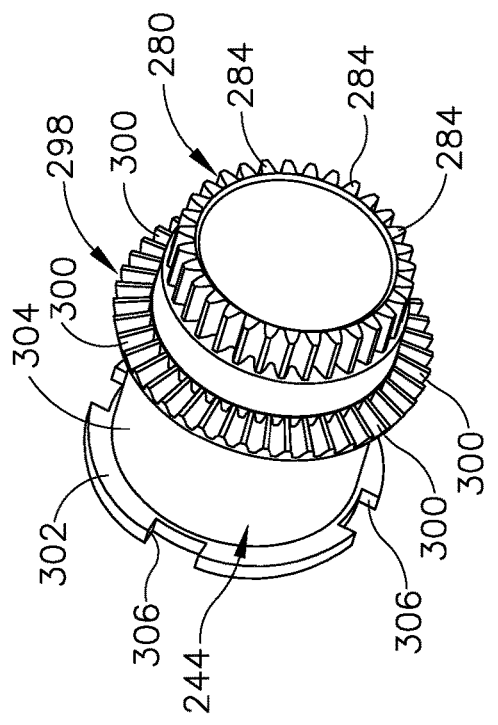
FIG. 26 depicts a rear perspective view of a drive drum of the dual sensitivity drive of FIG. 20.
Figure 29:
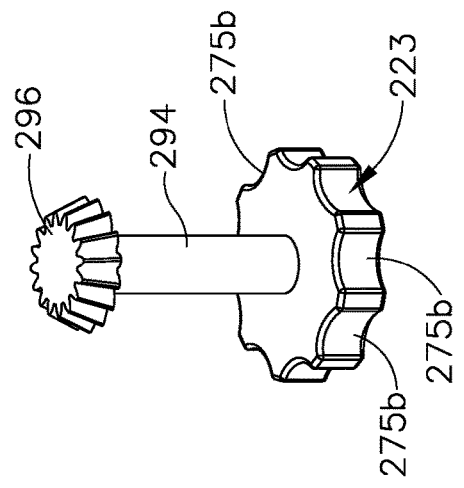
FIG. 29 depicts a lower perspective view of the high sensitivity articulation control knob of FIG. 28.
Figure 28:
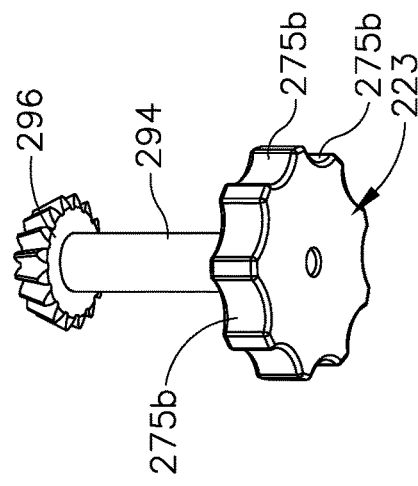
FIG. 28 depicts an upper perspective view of a high sensitivity articulation control knob of the dual sensitivity drive of FIG. 20.

In addition, lead screws (254, 256) are each respectively connected to translatable members (232, 233) via respective tensioners (266) as shown in FIGS. 18-19. Each tensioner (266) has a key (268) engaged with the respective translatable member (232, 233) to direct movement of translatable members (232, 233) distally or proximally along the longitudinal axis via high and low articulation control knobs (222, 223). However, each tensioner (266) also rotatably receives its respective lead screw (254, 256) within an annular channel (270) such that each lead screw (254, 256) and articulation drum (252) are collectively configured to be rotated via rotation control knob (224) (see FIG. 11) when rotating shaft assembly (212) without affecting articulation. By way of example, each tensioner (266) is defined by a C-shaped component (272), which includes key (268), and an annular component (274). Further details regarding articulation drum (252), lead screws (254, 256), and other various similarities with articulation control assembly (218) are described in U.S. patent application Ser. No. 14/688,663 entitled "Ultrasonic Surgical Instrument with Opposing Thread Drive for End Effector Articulation," filed on Apr. 16, 2015, now published as U.S. Pat. Pub. No. 2016/0302820, published on Oct. 20, 2016, the disclosure of which is incorporated by reference herein in its entirety.

On one hand, either of high and low articulation control knobs (222, 223) may be selectively rotated by the operator to articulate articulation section (130) (see FIG. 11) through transmission assembly (226) as shown in FIGS. 14-19. On the other hand, transmission assembly (226) is configured to inhibit inadvertent articulation of articulation control assembly (218) by operatively locking transmission assembly (226) when high and low articulation control knobs (222, 223) are not being rotated. In other words, rotation of either one of high and low articulation control knobs (222, 223) effectively unlocks articulation control assembly (218), otherwise transmission assembly (226) effectively locks articulation of articulation section (130) (see FIG. 11). By way of example, self-locking of transmission assembly (226) occurs because forces imposed on lead screws (254, 256) via shaft assembly (212) (e.g., when end effector (40) encounters transversely oriented loads imposed by anatomical structures or other surgical instruments, etc.) are incapable of providing sufficient mechanical advantage to rotate articulation drum (252). However, rotating articulation drum (252) via high and low articulation control knobs (222, 223) unlocks movement with sufficient mechanical advantage over lead screws (254, 256) to translate lead screws (254, 256) and articulate articulation section (130) (see FIG. 11). In the present example, articulation control knobs (222, 223) each have respective notches (275a, 275b) positioned angularly thereabout. Notches (275a, 275b) are configured to provide improved grip to the operator while manipulating the high and low articulation control knobs (222, 223).

FIGS. 20-21 show high and low ratio drives (227, 228) connected to high and low articulation control members (222, 223) for dual mode articulation as briefly discussed above. In the example shown in FIGS. 20-23, high ratio drive (227) includes a high face gear (276) having a plurality of teeth (278) extending downwardly from high articulation control knob (222). Teeth (278) are arranged in a starburst pattern. High face gear (276) is unitarily formed with high articulation control knob (222) in the present example. Alternatively, high face gear (276) may be rigidly connected to high articulation control knob (222) by another structure, such as a shaft. High face gear (276) is thus configured to be rotatably driven about the high transverse axis simultaneously with high articulation control knob (222).

As also shown in FIGS. 20-21 and FIGS. 24-27, high face gear (276) is operatively connected drive drum (244) via a spur gear (280) and a drive coupling (282). Spur gear (280) is an integral feature of drive drum (244), located at the proximal end of drive drum (244). Spur gear (280) has a plurality of teeth (284) projecting radially outwardly about the longitudinal axis of drive drum (244). Drive coupling (282) has a proximal gear (286), a distal gear (288), and a coupling shaft (290) extending rigidly therebetween. Proximal gear (286) is in the form of a spur gear; while distal gear (288) is in the form of a bevel gear. Gears (286, 288) rotate together unitarily with shaft (290). In particular, gears (286, 288) and shaft (290) are configured to rotate about an axis that is generally parallel to the longitudinal axis defined by shaft assembly (212) (see FIG. 11). High face gear (276) meshes with distal gear (288), while proximal gear (286) meshes with spur gear (280). Thus, coupling (282) is configured to transmit rotation of high articulation control knob (222) to drum (244), such that drum (244) will rotate in response to rotation of knob (222).

In order to provide a compact form factor to high ratio drive (227), distal gear (289) is nested within a hollow (292) of high articulation control knob (222). While high ratio drive (227) includes high face gear (276), spur gear (280), and drive coupling (282) for driving drive drum (244) as discussed herein, it will be appreciated that alternative mechanisms configured to direct movement of drive drum (244) and/or articulation drum (252). By way of example, high ratio drive (227) may alternatively include other mechanical and/or electrical assemblies for flexing shaft assembly (212). The invention is thus not intended to be unnecessarily limited to high ratio drive (227) of the present example.

As shown in FIGS. 20-21 and 26-29, low ratio drive (228) of the present example includes a low drive shaft (294) extending rigidly upwardly from low articulation control member (223) to a low drive gear (296) for engagement with a low face gear (298). Low drive gear (296) is in the form of a bevel gear and is rigidly connected to low drive shaft (294) such that low articulation control member (223), low drive shaft (294), and low drive gear (296) are configured to be simultaneously rotated bout the low transverse axis. Low face gear (298) is an integral feature of drive drum (244), located distal to spur gear (280). Low face gear (298) includes a plurality of teeth (300) projecting proximally in a starburst arrangement about the longitudinal axis of drive drum (244). Low face gear (298) meshes with low drive gear (296). While low face gear (298) and distal gear (288) are located in close proximity with each other in this example, it should be understood that gears (288, 298) do not actually mesh with each other in this example.

Since low face gear (298) meshes with low drive gear (296), rotation of low drive gear (296) via low articulation control member (223) and low drive shaft (294) will provide rotation of drive drum (244) about the longitudinal axis of drive drum (244). It should be understood that the bevel gear configuration of low drive gear (296) will provide this rotation despite drive drum (244) and low drive shaft (294) being oriented along respective axes that are angled 90 degrees from each other. While low ratio drive (228) includes low drive shaft (294), low drive gear (296), and low face gear (298) for driving drive drum (244) as discussed herein, it will be appreciated that alternative mechanisms configured to direct movement of drive drum (244) and/or articulation drum (252). By way of example, low ratio drive (228) may alternatively include other mechanical and/or electrical assemblies for flexing shaft assembly (212). The invention is thus not intended to be unnecessarily limited to exemplary low ratio drive (228) of the present example.

As noted above, drive drum (244), spur gear (280), and low face gear (298) are unitarily formed together in the present example and are thus configured to rotate collectively and simultaneously for transmitting rotation therethrough for driving articulation drum (252). Alternatively, one or more of drive drum (244), spur gear (280), and low face gear (298) may be formed separately and then affixed together via a securement, such as a separate fastener, integral clip, adhesive, or weld, etc. By way of further example, drive drum (244) includes a distal flange (304) and an annular body (304) proximally extending therefrom. Distal flange (302) defines a plurality of angularly spaced key slots (306) that are configured to engage a respective plurality of annularly spaced key tabs (308) (see FIG. 17) defined by a proximal end of articulation drum (252) (see FIG. 17) for driving rotation of articulation drum (252) (see FIG. 17). Furthermore, annular body (304) of drive drum (244) and spur gear (280) have approximately equivalent outer diameters. In contrast, low face gear (298) surrounds annular body (304) about the longitudinal axis such that annular body (304) has an outer diameter approximately equivalent to an inner diameter of low face gear (298).

Figure 30:
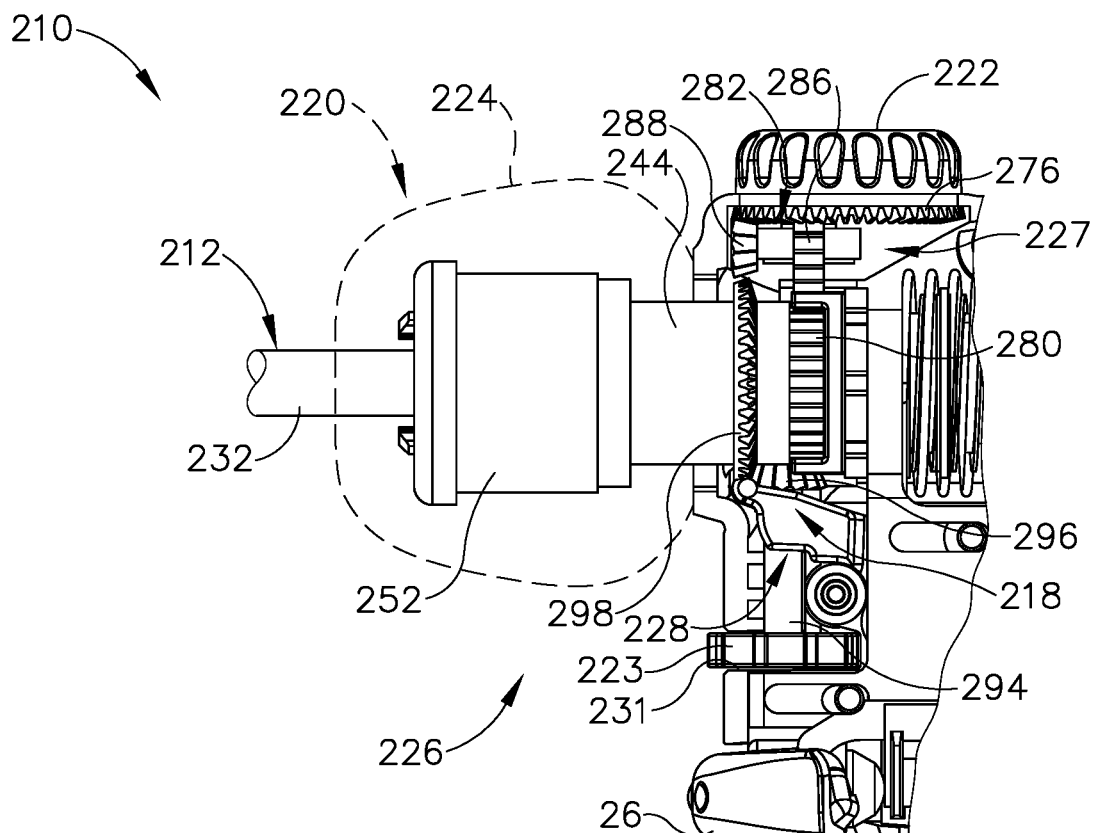
FIG. 30 depicts an enlarged side elevational view of the disposable assembly of FIG. 12, having various components removed for clarity.
Figure 31:
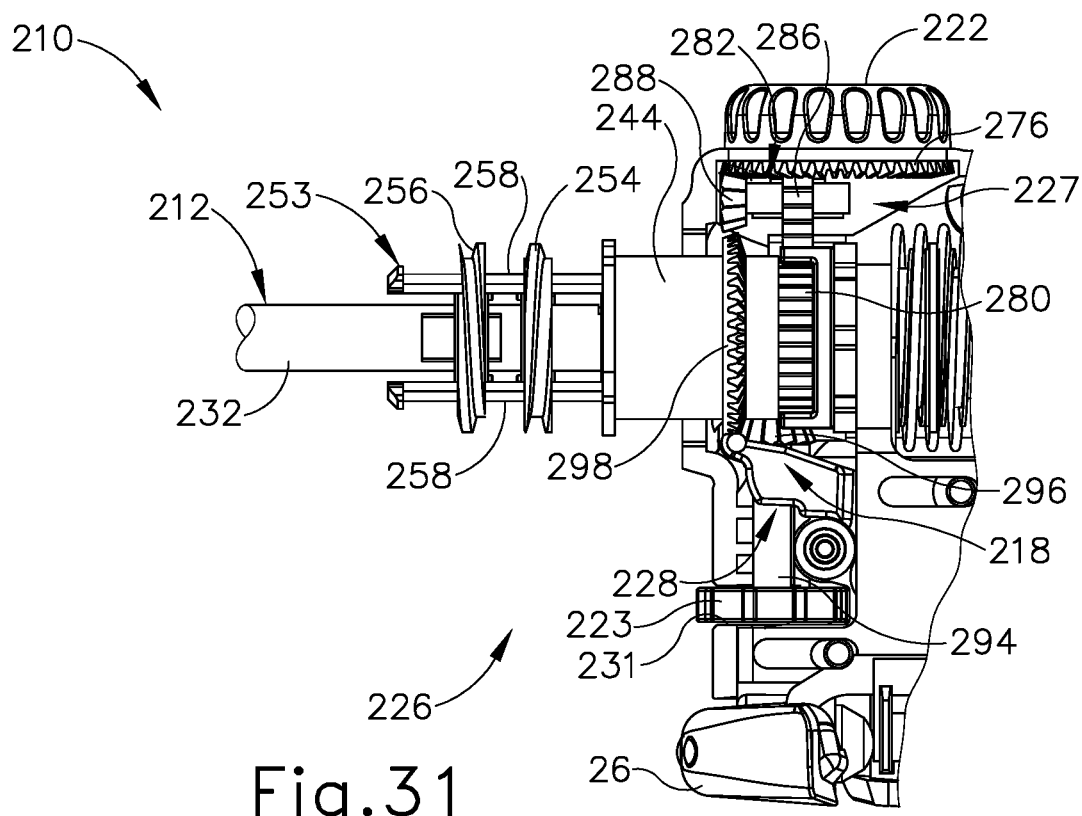
FIG. 31 depicts an enlarged side elevational view of the disposable assembly of FIG. 12, having various components removed for clarity, including an articulation drum removed for illustrating a straight configuration for a shaft assembly.
Figure 32:
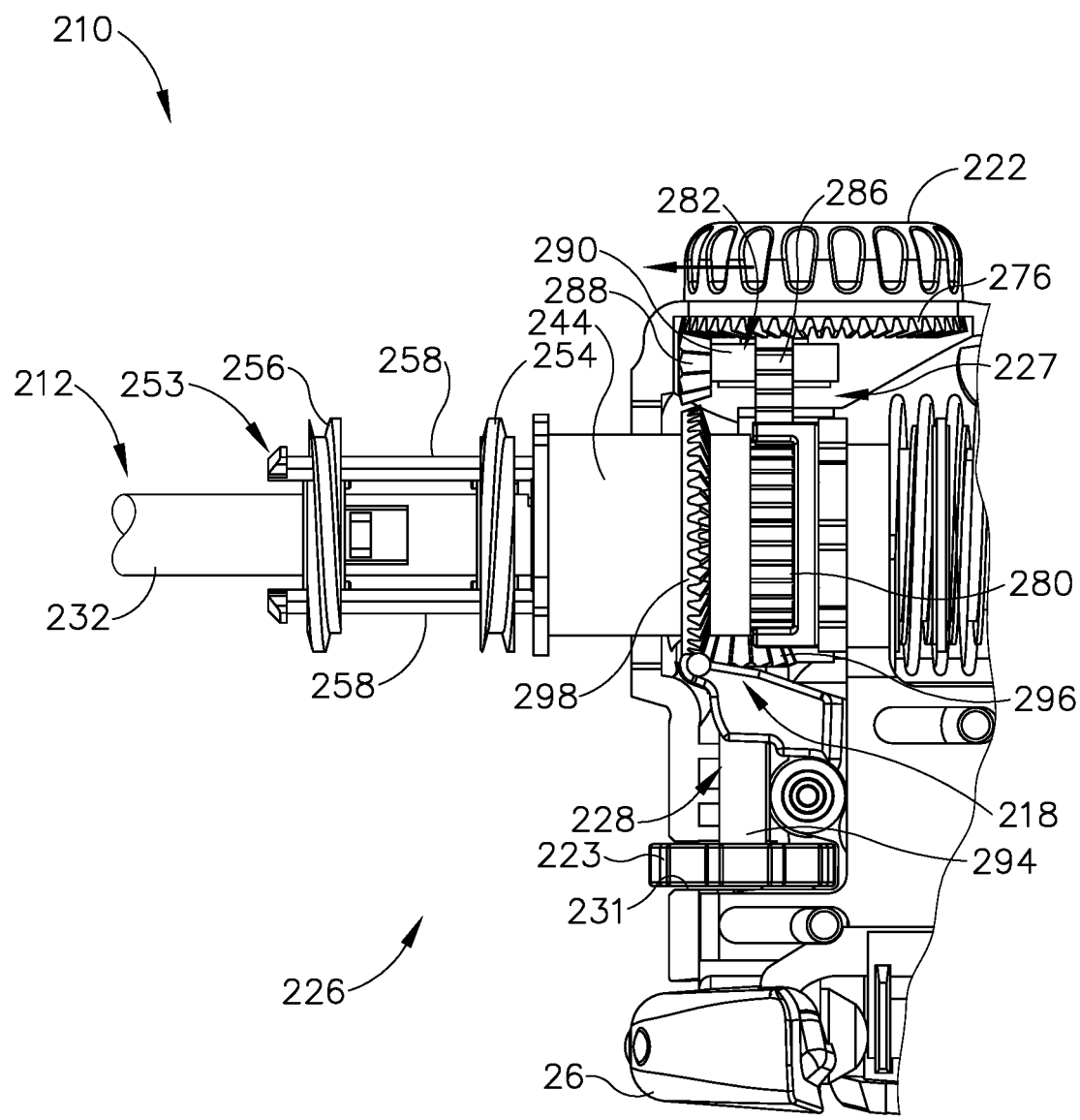
FIG. 32 depicts an enlarged side elevational view of the disposable assembly of FIG. 12, having various components removed for clarity, showing the low sensitivity articulation control knob having been manipulated to actuate the articulation section of the shaft assembly.

FIGS. 30-31 show articulation control assembly (218) in a straight configuration, but with articulation drum (252) removed to reveal lead screws (254, 256). As shown in FIG. 32, the operator manipulates high articulation control knob (222) clockwise (when viewed from above) for rightward articulation of articulation section (130) (see FIG. 11). In turn, high articulation control knob (222) drives coupling shaft (290) clockwise (when viewed from the view of the operator during use). Coupling shaft (290) engages spur gear (280) to direct drive drum (244) counterclockwise, which similarly directs articulation drum (252) counterclockwise. As articulation drum (252) rotates counterclockwise, proximal and distal inner threads (262, 264) translate proximal and distal lead screws (254, 256) longitudinally away from each other toward a desirable right configuration. High articulation control knob (222) thus operatively connects to drive drum (244) with high ratio drive (227) such that a predetermined amount of clockwise rotation of high articulation control knob (222) results in a relatively large degree of articulation of articulation section (130) (see FIG. 11). The operator may thus quickly and efficiently selectively move end effector (40) (see FIG. 11) toward tissue, but with the less sensitive high articulation control knob (222).

Figure 33:
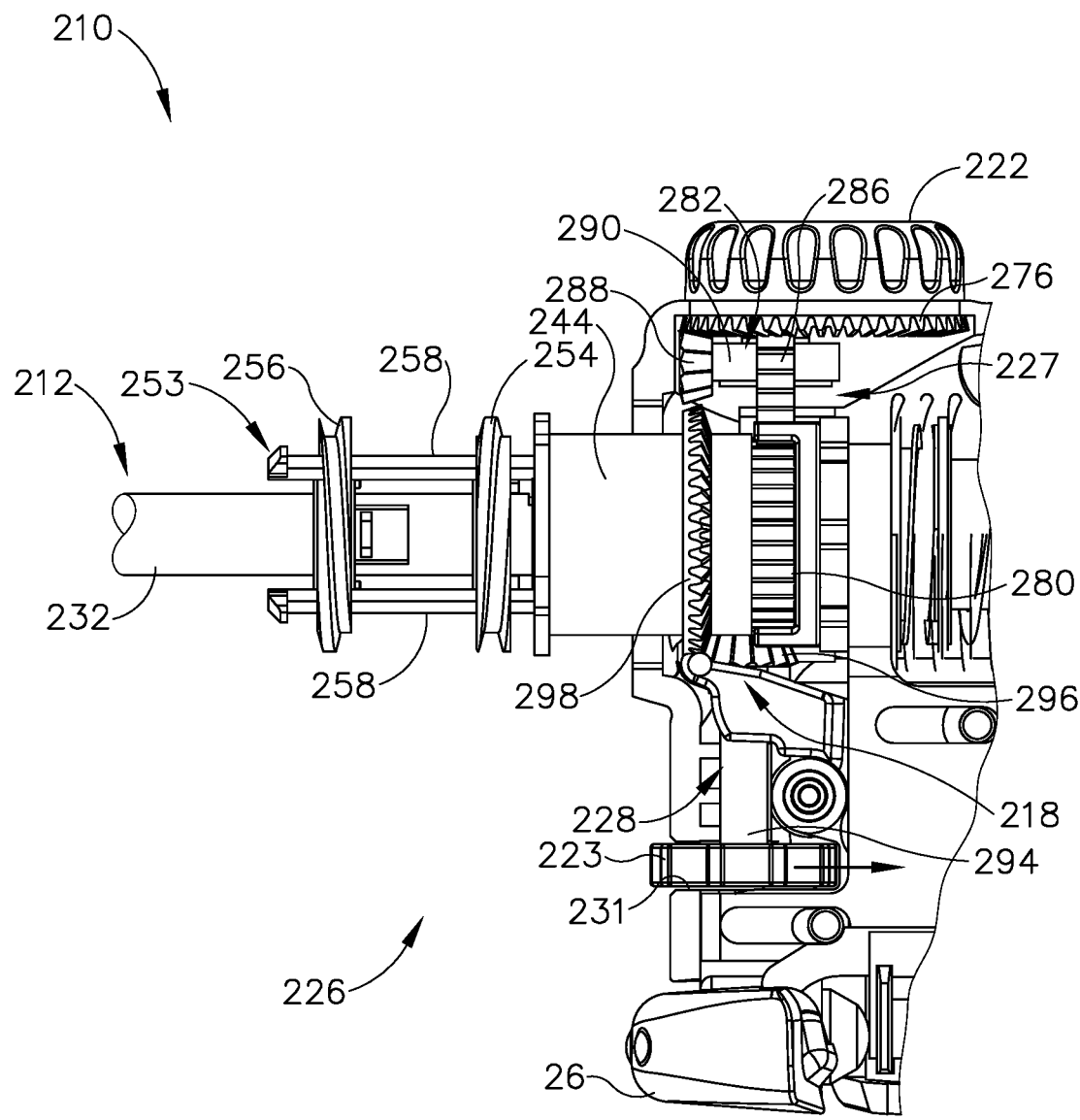
FIG. 33 depicts an enlarged side elevational view of the disposable assembly of FIG. 12, having various components removed for clarity, showing the high sensitivity articulation control knob having been manipulated to actuate the articulation section of the shaft assembly.

For finer adjustment of end effector (40) (see FIG. 11) relative to tissue, the operator manipulates low articulation control knob (223). In one example, the operator directs articulation section (130) (see FIG. 11) slightly leftward to the desired position shown in FIG. 33. To this end, the operator manipulates low articulation control knob (223) counterclockwise (when viewed from above) for leftward articulation of articulation section (130) (see FIG. 11). In turn, low articulation control knob (223) directs low drive gear (296) similarly counterclockwise. Low drive gear (296) engages low face gear (298) to direct drive drum (244) clockwise, which similarly directs articulation drum (252) clockwise. As articulation drum (252) rotates clockwise, proximal and distal inner threads (262, 264) translate proximal and distal lead screws (254, 256) longitudinally toward each other to the desirable right configuration. Low articulation control knob (223) thus operatively connects to drive drum (244) with low ratio drive (228) such that the predetermined amount of counterclockwise rotation of low articulation control knob (223) results in a relatively small degree of articulation of articulation section (130) (see FIG. 11). The operator may thus more accurately and precisely selectively move end effector (40) (see FIG. 11) toward tissue with the more sensitive low articulation control knob (223).

While the above description of describes clockwise manipulation of high articulation control knob (222) and counterclockwise manipulation of low control knob (223), counterclockwise and clockwise manipulation of high and low articulation control knobs (222, 223), respectively, will drive articulation control assembly (218) opposite from that described above. Furthermore, the operator may desire to manipulate high and low articulation control knobs (222, 223) in any desirable order for treating the patient. Alternatively, the operator may desire to only use one of the high and low articulation control knobs (222, 223). It should therefore be understood that the use of surgical instrument (210) is not intended to be unnecessarily limited to the exemplary use described herein. Furthermore, while the above described articulation control assembly (218) is dual mode with two distinct sensitivities derived from two high and low ratio drives (227, 228), it will be appreciated that additional modes and drives may be incorporated into articulation control assembly (218) for additional sensitivities as found to be desirable.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a shaft assembly defining a longitudinal axis, wherein the shaft assembly includes: (i) a proximal end portion, (ii) a distal end portion having an end effector, and (iii) an articulation section configured to deflect the end effector from the longitudinal axis; and (b) an articulation control assembly connected to the proximal end portion of the shaft assembly, wherein the articulation control assembly includes: (i) a first articulation control member, (ii) a second articulation control member, and (iii) a transmission assembly comprising: (A) a high ratio drive, wherein the high ratio drive is configured to drive the articulation section to deflect the end effector at a high rate of articulation in response to actuation of the first articulation control member, and (B) a low ratio drive, wherein the low ratio drive is configured to drive the articulation section to deflect the end effector at a low rate of articulation in response to actuation of the second articulation control member.

Example 2

The surgical instrument of Example 1, wherein the first articulation control member is rotatably mounted relative to the shaft assembly and is configured to be rotatably manipulated, and wherein the second articulation control member is rotatably mounted relative to the shaft assembly and is configured to be rotatably manipulated.

Example 3

The surgical instrument of any one or more of Examples 1 through 2, wherein the transmission assembly further includes a drive member operatively connected to the articulation section and engaged with each of the high and low ratio drives, wherein the drive member is configured to be driven by each of the high and low ratio drives and transmit movement from the high and low ratio drives toward the articulation section for deflecting the distal end portion from the longitudinal axis.

Example 4

The surgical instrument of Example 3, wherein the drive member comprises a drive drum extending along the longitudinal axis, wherein the drive drum is configured to be rotatably driven by each of the high and low ratio drives about the longitudinal axis.

Example 5

The surgical instrument of Example 4, wherein the low ratio drive includes a first face gear and the high ratio drive includes a spur gear, wherein the first face gear is rigidly connected to the drive drum and extends about the longitudinal axis, wherein the spur gear is rigidly connected to the drive drum and extends about the longitudinal axis, and wherein the first face and spur gears are configured to simultaneously rotate about the longitudinal axis with the drive drum.

Example 6

The surgical instrument of Example 5, wherein the first face gear is configured to be rotatably driven via the second articulation control member, and wherein the spur gear is configured to be rotatably driven via the first articulation control member.

Example 7

The surgical instrument of Example 6, wherein the second articulation control member comprises a low articulation control knob, and wherein the first articulation control member comprises a high articulation control knob.

Example 8

The surgical instrument of Example 7, wherein the low and high articulation control knobs are respectively configured to rotate about a low transverse axis and a high transverse axis, and wherein each of the low and high transverse axes are oriented perpendicular to the longitudinal axis.

Example 9

The surgical instrument of Example 8, wherein the low ratio drive further includes a low bevel drive gear, wherein the low articulation control knob is rigidly connected to the low bevel drive gear via a low drive shaft, wherein each of the low bevel drive gear and the low drive shaft are configured to rotate about the low transverse axis, wherein the first face gear comprises a first bevel face gear, and wherein the first bevel face gear engages the low drive bevel gear to be rotatably driven by the low drive bevel gear.

Example 10

The surgical instrument of any one or more of Examples 7 through 9, wherein the high ratio drive further includes a second face gear, wherein the second face gear rigidly extends from the high articulation control knob, and wherein the second face gear is configured to rotate about the high transverse axis.

Example 11

The surgical instrument of Example 10, wherein the high ratio drive further includes a drive coupling, wherein the drive coupling is engaged with each of the second face gear and the spur gear and is configured to be rotatably driven by the second face gear and thereby rotatably drive the spur gear.

Example 12

The surgical instrument of any one or more of Examples 3 through 11, wherein the transmission assembly further includes: (A) an articulation drum configured to rotate about the longitudinal axis, wherein the articulation drum includes a plurality of inner threads about the longitudinal axis, and (B) at least one lead screw engaged with the plurality of inner threads and configured to translate along the longitudinal axis upon rotation of the articulation drum for flexing the articulation section, wherein the high and low ratio drives are operatively connected to the articulation drum such that selective manipulation of the high and second articulation control members is configured to rotate the articulation drum for flexing the articulation section via the at least one lead screw.

Example 13

The surgical instrument of Example 12, wherein the at least one lead screw is configured to self-lock without selective manipulation of the high and second articulation control members to thereby inhibit flexing of the articulation section and unlock with selective manipulation of the high and second articulation control members to thereby flex the articulation section.

Example 14

The surgical instrument of any one or more of Examples 1 through 13, further comprising an end effector located at the distal end portion of the shaft assembly, wherein the end effector comprises an ultrasonic blade, wherein the shaft assembly further comprises an acoustic waveguide, wherein the acoustic waveguide is coupled with the ultrasonic blade, wherein the acoustic waveguide extends through the proximal end portion, the articulation section, and the distal end portion.

Example 15

The surgical instrument of any one or more of Examples 1 through 14, further comprising a disposable assembly and a handle assembly portion, wherein the disposable assembly includes the shaft assembly and the articulation control assembly, and wherein the disposable assembly is configured to removably connect to the handle assembly portion.

Example 16

An articulation control assembly for a surgical instrument, comprising: (a) a body; (b) a shaft assembly extending distally from the body, the shaft assembly including an articulation section, wherein the shaft assembly defines a longitudinal axis; (c) an end effector located at a distal end of the shaft assembly, wherein the articulation section is operable to selectively deflect the end effector away from the longitudinal axis; (d) a first articulation control member; (e) a second articulation control member; and (f) a transmission assembly operatively connected to the body, the transmission assembly comprising: (i) a high ratio drive, wherein the high ratio drive is configured to drive the articulation section to deflect the end effector from the longitudinal axis at a high rate of articulation in response to actuation of the first articulation control member, and (ii) a low ratio drive, wherein the low ratio drive is configured to drive the articulation section to deflect the end effector from the longitudinal axis at a low rate of articulation in response to actuation of the second articulation control member.

Example 17

The articulation control assembly of Example 16, wherein the articulation section is configured to flex to thereby deflect the end effector away from the longitudinal axis.

Example 18

The articulation control assembly any one or more of Examples 16 through 17, wherein the first articulation control member comprises a first rotatable member, wherein the second articulation control member comprises a second rotatable member, first and second rotatable members are rotatable independently of each other.

Example 19

The articulation control assembly of Example 18, wherein the first and second rotatable members are rotatable about respective axes that are each perpendicular to the longitudinal axis.

Example 20

A method of operating an instrument, wherein the instrument comprises: (a) a shaft assembly defining a longitudinal axis, wherein the shaft assembly has an articulation section; (b) an end effector secured to the shaft assembly; (c) a first articulation control, wherein the first articulation control is operable to actuate the articulation section to thereby deflect the end effector away from the longitudinal axis at a first rate of articulation; and (d) a second articulation control, wherein the second articulation control is operable to actuate the articulation section to thereby deflect the end effector away from the longitudinal axis at a second rate of articulation; wherein the method comprises: (a) inserting the distal end of the shaft assembly into a patient while the articulation section is in a non-articulated state, such that the end effector is aligned with the longitudinal axis; (b) manipulating the first articulation control to provide coarse adjustment of the articulation section, thereby deflecting the end effector away from the longitudinal axis at a first rate of articulation; and (c) manipulating the second articulation control to provide fine adjustment of the articulation section, thereby deflecting the end effector away from the longitudinal axis at a second rate of articulation, wherein the second rate of articulation is lower than the first rate of articulation.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:
1. A surgical instrument, comprising:
 (a) a shaft assembly, including:
  (i) a proximal end portion defining a longitudinal axis,
  (ii) a distal end portion configured to have an end effector extending distally therefrom, and

(iii) an articulation section configured to deflect the distal end portion away from the longitudinal axis and relative to the proximal end portion; and (b) an articulation control assembly operatively connected to the articulation section of the shaft assembly, wherein the articulation control assembly includes:
(i) at least one articulation control member configured to be selectively actuated by an operator, and
(ii) a transmission assembly operatively connected to the at least one articulation control member and having a high ratio drive and a low ratio drive,
wherein the articulation control assembly is configured to select one of the high and low ratio drives to thereby drive the articulation section to respectively deflect the distal end portion at a high rate of articulation or a low rate of articulation in response to actuation of the at least one articulation control member.

2. The surgical instrument of claim 1, wherein the at least one articulation control member further includes a first articulation control member and a second articulation control member, wherein the high ratio drive is configured to drive the articulation section to deflect the distal end portion at the high rate of articulation in response to actuation of the first articulation control member, and wherein the low ratio drive is configured to drive the articulation section to deflect the distal end portion at the low rate of articulation in response to actuation of the second articulation control member.

3. The surgical instrument of claim 1, wherein the shaft assembly further includes an acoustic waveguide extending through the articulation section, and wherein the acoustic waveguide is configured to communicate an ultrasonic energy therealong.

4. The surgical instrument of claim 3, further comprising an end effector having an ultrasonic blade projecting distally from the distal end portion of the shaft assembly, and wherein the ultrasonic blade is in acoustic communication with the acoustic waveguide.

5. The surgical instrument of claim 1, wherein the at least one articulation control member is rotatably mounted relative to the shaft assembly and configured to be rotatably manipulated by the operator.

6. The surgical instrument of claim 1, wherein the transmission assembly further includes a drive member operatively connected to the articulation section and engaged with each of the high and low ratio drives, and wherein the drive member is configured to be driven by each of the high and low ratio drives and transmit movement from the high and low ratio drives toward the articulation section for deflecting the distal end portion from the longitudinal axis.

7. The surgical instrument of claim 6, wherein the drive member comprises a drive drum, and wherein the drive drum is configured to be rotatably driven by each of the high and low ratio drives.

8. The surgical instrument of claim 7, wherein the drive drum extends along the longitudinal axis and is configured to be rotatably driven about the longitudinal axis by each of the high and low ratio drives.

9. The surgical instrument of claim 8, wherein the low ratio drive includes a first face gear and the high ratio drive includes a spur gear, wherein the first face gear is rigidly connected to the drive drum and extends about the longitudinal axis, wherein the spur gear is rigidly connected to the drive drum and extends about the longitudinal axis, and wherein the first face and spur gears are configured to simultaneously rotate about the longitudinal axis with the drive drum.

10. The surgical instrument of claim 9, wherein the first face gear and the spur gear are configured to be rotatably driven via the at least one articulation control member.

11. The surgical instrument of claim 10, wherein the low ratio drive further includes a low bevel drive gear, wherein the first face gear comprises a first bevel face gear, and wherein the first bevel face gear engages the low bevel drive gear to be rotatably driven.

12. The surgical instrument of claim 10, wherein the high ratio drive further includes a second face gear, and wherein the second face gear is configured to be rotatably driven.

13. The surgical instrument of claim 12, wherein the high ratio drive further includes a drive coupling, wherein the drive coupling is engaged with each of the second face gear and the spur gear and is configured to be rotatably driven by the second face gear and thereby rotatably drive the spur gear.

14. The surgical instrument of claim 1, wherein the transmission assembly further includes:
(A) an articulation drum including a plurality of inner threads, and
(B) at least one lead screw engaged with the plurality of inner threads and configured to translate upon rotation of the articulation drum for flexing the articulation section,
wherein the high and low ratio drives are operatively connected to the articulation drum such that selective manipulation of the at least one articulation control member is configured to rotate the articulation drum for flexing the articulation section via the at least one lead screw.

15. The surgical instrument of claim 14, wherein the at least one lead screw is configured to self-lock without selective manipulation of the at least one articulation control member to thereby inhibit flexing of the articulation section and unlock with selective manipulation of the at least one articulation control member to thereby flex the articulation section.

16. The surgical instrument of claim 1, further comprising an end effector located at the distal end portion of the shaft assembly, wherein the end effector comprises an ultrasonic blade, wherein the shaft assembly further comprises an acoustic waveguide, wherein the acoustic waveguide is coupled with the ultrasonic blade, wherein the acoustic waveguide extends through the proximal end portion, the articulation section, and the distal end portion.

17. A surgical instrument, comprising:
(a) an end effector;
(b) a shaft assembly proximally extending from the end effector, including:
(i) a proximal end portion defining a longitudinal axis,
(ii) a distal end portion having the end effector distally projecting therefrom, and
(iii) an articulation section configured to deflect the end effector relative to the longitudinal axis; and
(c) a transmission assembly operatively connected to the articulation section and configured to receive a predetermined input and thereby direct deflection of the end effector via the articulation section, wherein the transmission assembly includes:
(i) a high ratio drive configured to receive the predetermined input and drive the articulation section to deflect the end effector at a high rate of articulation in response to the predetermined input, and (ii) a low ratio drive configured to drive the articulation section to deflect the end effector at a low rate of articulation in response to the predetermined input.

18. The surgical instrument of claim 17, wherein the end effector includes an ultrasonic blade, and wherein the shaft assembly further includes an acoustic waveguide extending from the proximal end portion through the articulation section to the distal end portion and in acoustic communication with the ultrasonic blade.

19. The surgical instrument of claim 18, wherein the high ratio drive is configured to receive the predetermined input and deflect the end effector a first distance from the longitudinal axis, wherein the low ratio drive is configured to receive the predetermined input and deflect the end effector a second distance from the longitudinal axis, and wherein the first distance based on the predetermined input is greater than the second distance based on the predetermined input.

20. A method of deflecting an end effector of a surgical instrument, wherein the surgical instrument includes (a) the end effector; (b) a shaft assembly proximally extending from the end effector, including: (i) a proximal end portion defining a longitudinal axis, (ii) a distal end portion having the end effector distally projecting therefrom, and (iii) an articulation section configured to deflect the end effector relative to the longitudinal axis; and (c) a transmission assembly operatively connected to the articulation section and configured to receive a predetermined input and thereby direct deflection of the end effector via the articulation section, wherein the transmission assembly includes: (i) a high ratio drive configured to receive the predetermined input and drive the articulation section to deflect the end effector at a high rate of articulation in response to the predetermined input, and (ii) a low ratio drive configured to drive the articulation section to deflect the end effector at a low rate of articulation in response to the predetermined input, the method comprising:
   (a) selecting the high ratio drive or the low ratio drive from among at least the high ratio drive and the low ratio drive; and
   (b) providing the predetermined input to the transmission assembly and thereby deflecting the end effector relative to the longitudinal axis.

\* \* \* \* \*